(12) United States Patent
Los

(10) Patent No.: US 12,329,891 B2
(45) Date of Patent: *Jun. 17, 2025

(54) MODULAR MEDICAL FLUID MANAGEMENT ASSEMBLIES, MACHINES AND METHODS

(71) Applicants: BAXTER INTERNATIONAL INC., Deerfield, IL (US); BAXTER HEALTHCARE SA, Glattpark (CH)

(72) Inventor: Oleg Los, Buffalo Grove, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/208,604

(22) Filed: Jun. 12, 2023

(65) Prior Publication Data

US 2023/0321330 A1 Oct. 12, 2023

Related U.S. Application Data

(63) Continuation of application No. 16/983,621, filed on Aug. 3, 2020, now Pat. No. 11,672,894, which is a
(Continued)

(51) Int. Cl.
 *A61M 1/26* (2006.01)
 *A61M 1/14* (2006.01)
 (Continued)

(52) U.S. Cl.
 CPC .......... *A61M 1/267* (2014.02); *A61M 1/1639* (2014.02); *A61M 1/3621* (2013.01);
 (Continued)

(58) Field of Classification Search
 CPC ........ A61M 2205/12; A61M 2205/128; A61M 1/1639; A61M 1/267; A61M 1/14;
 (Continued)

(56) References Cited

U.S. PATENT DOCUMENTS

| 3,656,873 A | 4/1972 | Schiff |
| 4,983,102 A | 1/1991 | Swain |

(Continued)

OTHER PUBLICATIONS

International Search Report PCT/US18/53978 mailing date Jan. 10, 2019—3 pages.

(Continued)

*Primary Examiner* — Adam Marcetich
(74) *Attorney, Agent, or Firm* — K&L Gates LLP

(57) ABSTRACT

A medical fluid management assembly includes a pneumatic manifold, a pump engine, a valve engine, and a fluid manifold. The pneumatic manifold includes a plurality of pneumatic passageways and a plurality of pneumatic connectors. The pump engine includes a pump chamber and the valve engine includes a valve chamber. Each of the pump engine and valve engine includes a pneumatic connector mated sealingly and releaseably with one of the pneumatic connectors of the pneumatic manifold. Additionally, each of the pump engine and valve engine includes a fluid connector. The fluid manifold includes a plurality of fluid pathways and a plurality of fluid connectors mated sealingly and releaseably with the fluid connectors of the pump engine and the valve engine.

20 Claims, 16 Drawing Sheets

Related U.S. Application Data continuation of application No. 15/723,773, filed on Oct. 3, 2017, now Pat. No. 10,729,839.

(51) Int. Cl.
*A61M 1/16* (2006.01)
*A61M 1/34* (2006.01)
*A61M 1/36* (2006.01)
*A61M 39/24* (2006.01)

(52) U.S. Cl.
CPC ............. *A61M 39/24* (2013.01); *A61M 1/155* (2022.05); *A61M 1/1565* (2022.05); *A61M 1/1656* (2013.01); *A61M 1/3413* (2013.01); *A61M 1/3424* (2014.02); *A61M 1/36225* (2022.05); *A61M 1/362265* (2022.05); *A61M 1/3626* (2013.01); *A61M 1/3638* (2014.02); *A61M 1/3656* (2014.02); *A61M 1/3672* (2013.01); *A61M 2205/12* (2013.01); *A61M 2205/3375* (2013.01)

(58) Field of Classification Search
CPC .............. A61M 1/1656; A61M 60/851; A61M 1/3621; A61M 2205/122; A61M 60/37; A61M 1/1601

See application file for complete search history.

(56) References Cited

U.S. PATENT DOCUMENTS

| | | |
|---|---|---|
| 5,002,471 A | 3/1991 | Perlov |
| 6,234,191 B1 | 5/2001 | Clark |
| 6,317,977 B1 | 11/2001 | Iijima |
| 2003/0220598 A1 | 11/2003 | Busby et al. |
| 2004/0019313 A1 | 1/2004 | Childers |
| 2005/0131332 A1 | 6/2005 | Kelly et al. |
| 2007/0205384 A1 | 9/2007 | Kurosawa |
| 2007/0278155 A1 | 12/2007 | Lo et al. |
| 2008/0058697 A1 | 3/2008 | Kamen et al. |
| 2008/0077068 A1 | 3/2008 | Orr |
| 2008/0202591 A1 | 8/2008 | Grant |
| 2009/0008311 A1 | 1/2009 | Lee |
| 2009/0012449 A1 | 1/2009 | Lee |
| 2009/0012461 A1 | 1/2009 | Childers et al. |
| 2009/0098407 A1 | 4/2009 | Minegishi |
| 2009/0112151 A1 | 4/2009 | Chapman et al. |
| 2009/0198174 A1 | 8/2009 | Childers |
| 2011/0071465 A1 | 3/2011 | Wang |
| 2013/0020237 A1 | 1/2013 | Wilt |
| 2014/0251450 A1 | 9/2014 | Hettinger |
| 2014/0257176 A1 | 9/2014 | Childers et al. |
| 2014/0322053 A1 | 10/2014 | van der Merwe |
| 2015/0306294 A1 | 10/2015 | Jansson et al. |
| 2016/0239025 A1 | 8/2016 | van der Merwe |
| 2017/0227525 A1 | 8/2017 | Griffith et al. |
| 2017/0326282 A1 | 11/2017 | Wilt |

OTHER PUBLICATIONS

Written Opinion PCT/US18/53978 mailing date Jan. 10, 2019—9 pages.

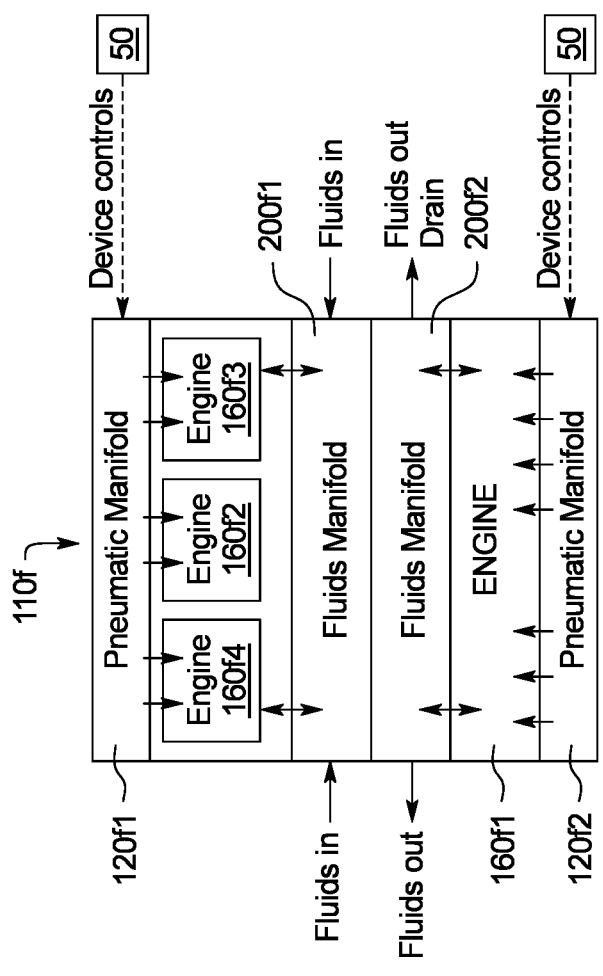
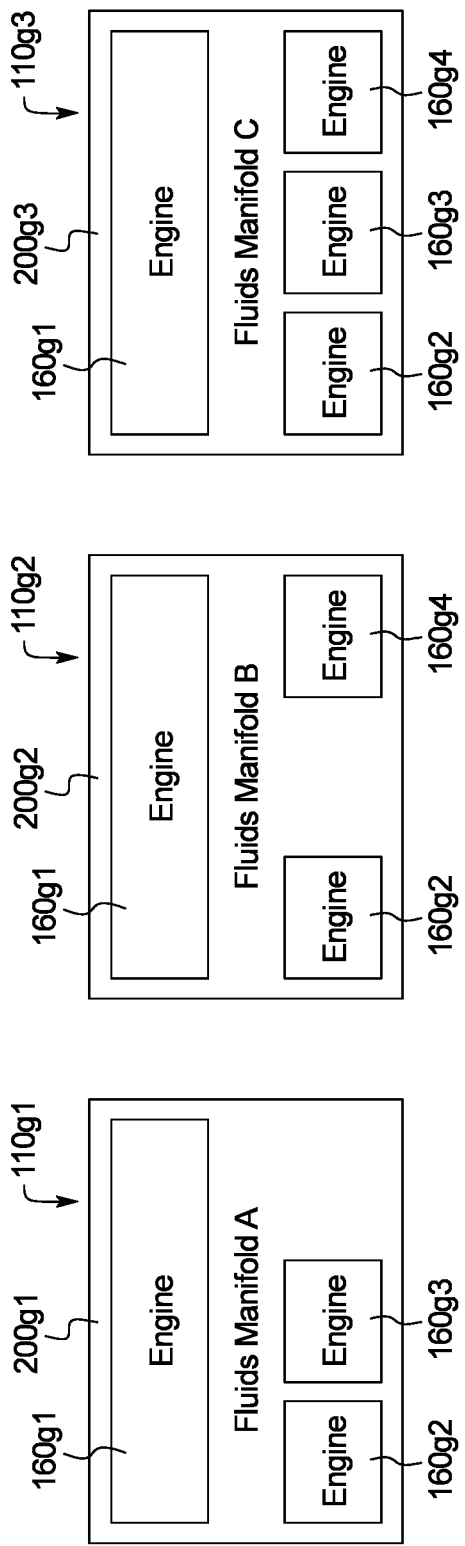

MODULAR MEDICAL FLUID MANAGEMENT ASSEMBLIES, MACHINES AND METHODS

PRIORITY CLAIM

This application claims priority to and the benefit as a continuation application of U.S. patent application Ser. No. 16/983,621, now U.S. Pat. No. 11,672,894, filed Aug. 3, 2020, which is a continuation application of U.S. patent application Ser. No. 15/723,773, now U.S. Pat. No. 10,729,839, filed Oct. 3, 2017, the entire contents of which are hereby incorporated by reference and relied upon.

CROSS-REFERENCE TO RELATED APPLICATION

This application shares a common written description and drawings with U.S. patent application Ser. No. 15/723,921, now U.S. Pat. No. 10,722,635, entitled "Modular Medical Fluid Management Assemblies and Associated Machines and Methods", filed concurrently with U.S. patent application Ser. No. 15/723,773 on Oct. 3, 2017.

BACKGROUND

The present disclosure relates generally to fluid management devices, systems and methods. More specifically, the present disclosure relates to fluid management devices, systems and methods for medical fluid delivery, such as blood, dialysis fluid, substitution fluid or intravenous drug delivery.

Due to various causes, a person's renal system can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products than a patient receiving less frequent but perhaps longer treatments. A patient receiving more frequent treatments does not experience as much of a down cycle as does an in-center patient, who has built-up two or three days worth of toxins prior to a treatment. In certain areas, the closest dialysis center can be many miles from the patient's home causing door-to-door treatment time to consume a large portion of the day. HHD can take place overnight or during the day while the patient relaxes, works or is otherwise productive.

Another type of kidney failure therapy is peritoneal dialysis, which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid solution bags.

APD machines pump used or spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

In any of the above modalities using an automated machine, it is desirable to provide a unit that is safe, reliable, performs well, is cost effective and reduces disposable waste if possible. Regarding reliability and safety, it is desirable that the machine operates within safe limits, but that the limits are diverse enough to allow the machine to operate without constant alarming or interruption due, for example, to a sensed parameter falling out of a range that has been set too narrowly. Reliability also depends upon robustness, e.g., making working and/or process fluid connections and seals that are easy to produce and that hold up under pressure. Performance involves being able to meet treatment goals and with overall operability including ease of setup and control. Cost effectiveness and disposable waste are related. In many instances, payment for treatment using the machines includes reimbursement. In such case, or in any case, reducing cost of disposable waste by reducing the amount of disposable items and/or enabling reuse of disposable items is desirable.

An automated medical fluid machine improving at least some of the above measurables is needed accordingly. For example, it may be desirable to make the medical fluid machine simpler, more modular, less expensive to manufacture, easier to assemble or disassemble, e.g., at home, and/or easier to maintain. Making components of the medical fluid machine modular, for example, allows parts and subassemblies to be used in future generation machines and related products.

SUMMARY

The examples described herein disclose automated systems and methods applicable, for example, to fluid delivery for: plasmapheresis, hemodialysis ("HD"), hemofiltration ("HF") hemodiafiltration ("HDF"), continuous renal replacement therapy ("CRRT"), apheresis, autotransfusion, hemofiltration for sepsis, and extracorporeal membrane oxygenation ("ECMO") treatments. The systems and methods described herein may also be applicable to peritoneal dialysis ("PD") and to intravenous drug delivery. These modalities may be referred to collectively or generally individually as medical fluid delivery.

Moreover, each of the assemblies, machines and methods described herein may be used with clinical or home-based applications. For example, the assemblies may be employed in in-center HD, HF or HDF machines, which run throughout the day. Alternatively, the assemblies may be used with home HD, HF or HDF machines, which are operated at the patient's convenience. One such home system that may be modified according to the present disclosure is described in U.S. Pat. No. 8,029,454 ("the '454 Patent"), issued Oct. 4, 2011, entitled "High Convection Home Hemodialysis/Hemofiltration And Sorbent System", filed Nov. 4, 2004, assigned to the assignee of the present application, the entire contents of which are incorporated herein by reference and relied upon.

In the present disclosure, a modular fluid management assembly, machine and method are provided. The modular fluid assembly is operated pneumatically in one embodiment. The assemblies may employ three primary components, namely, a pump and valve component (which may be referred to herein as a pump and valve engine), a pneumatic manifold, and a fluid (e.g., blood, dialysis fluid, liquid concentrate and/or water) manifold. The pump and valve component or engine in an embodiment contacts both fluid and air. The pneumatic manifold in an embodiment contacts only air, assuming no fluid leaks. The fluid manifold in an embodiment contacts only fluid, assuming no entrained air and no air leaks.

The pump and valve engine in an embodiment includes an air side and a fluid side, which are separated by a flexible membrane (referring to any of a flexible membrane, sheet or diaphragm) or by multiple flexible membranes sealed to one or more rigid structure. The pneumatic manifold is located on, e.g., coupled to, the air side of the pump and valve engine, while the fluid manifold is located on, e.g., coupled to, the fluid side of the manifold. In an embodiment, the air side of the engine defines pump and valve ports that extend into sealed communication with respective pump and valve recesses defined by the pneumatic manifold. In an embodiment, the fluid side of the engine defines pump and valve ports that extend into sealed communication with respective pump and valve recesses defined by the pneumatic manifold. The ports and recesses for the pump and valve engine and either one or both of the air and/or fluid manifolds may be reversed alternatively.

In an embodiment, the pneumatic manifold is made of a machined or molded material, such as metal or plastic and is reusable and generally not disposable. The machined pneumatic manifold may, for example, include multiple machined plates sealed together via a compressible gasket. One or more of the plates may have machined pneumatic passageways that greatly reduce the amount of pneumatic tubing needed to deliver positive and negative pneumatic pressure (or vent to atmosphere) to desired different locations of the pump and valve engine. Because the pneumatic manifold is not reusable and may contain many narrow machined pneumatic passageways, it is important to prevent fluid from leaking into the pneumatic manifold. To do so, multiple flexible membranes may be used in concert in the pump and valve engine. The additional flexible membrane(s) provides redundancy against fluid leaks, greatly reducing the chance that fluid, such as dialysis fluid or water, will enter the pneumatic manifold.

The pump and valve engine and the fluid manifold touch process fluid, such as dialysis fluid and/or water and are therefore disposable. Disposable may mean single use or may include multiple uses with a disinfection procedure performed in between uses. Because the engine and fluid manifold are disposable, they are likely made of a biocompatible, rigid plastic or other relatively inexpensive, liquid-tight material and are manufactured using mass production method, such as injection molding, for example. As mentioned above, the pump and valve engine will have one or more flexible membrane for performing the pumping and valving functions. The one or more flexible membrane may be made of a flexible rubber or plastic, such as silicone or polyvinyl chloride ("PVC"). The one or more flexible membrane may be solvent bonded, radio frequency welded, heat sealed and/or mechanically clamped to the rigid portion of the pump and valve engine.

The pump and valve engine may provide additional fluid storage vessels, such as balance chambers, a water accumulation chamber, one or more mixing chamber, and/or a water or dialysis fluid dearation chamber, sometimes called an airtrap. Each of the balance chambers, water accumulation chamber, mixing chamber and water or dialysis fluid dearation chamber differs from the pumps and valves in that they are not connected to the pneumatic manifold and instead include one or more connection to the fluid manifold. The balance chamber balances the flow of fresh and used dialysis fluid to and from the blood circuit, e.g., to and from a dialyzer. Two balance chambers may be provided so that fresh and used fluid flow relatively constantly to and from the blood circuit. The water accumulator stores a bolus of purified water in case of a temporary increased demand. The balance chambers and water accumulator may each employ a flexible membrane. The mixing chamber mixes water and a concentrate, such as a liquid acid concentrate, or water mixed with a concentrate, such as a powdered bicarbonate concentrate with an acid concentrate. The dearation chamber is shaped to remove and collect air from water or dialysis fluid flowing through the chamber.

The rigid, e.g., plastic, fluid manifold does not require a flexible membrane in one embodiment. The fluid manifold defines fluid pathways, e.g., rigid fluid pathways, which lead to inlet and outlet ports. The fluid manifold may also sealingly and removeably accept fluidic components, such as an ultrafilter with the goal of eliminating fluidic tubing as much as possible. It is contemplated that fluidic tubing may be optimized down to tubing for: (i) a purified water inlet, (ii) a liquid concentrate inlet, (iii) a fresh dialysis fluid inlet to the extracorporeal circuit (e.g., dialyzer), (iv) a used dialysis fluid outlet from the extracorporeal circuit (e.g., dialyzer), (v) a fresh dialysis fluid inlet to a dialysis fluid holding tank, (vi) a fresh dialysis fluid outlet from the dialysis fluid holding tank, and (vii) a drain line, wherein the drain line may be connected to a separate drain fluid manifold, which is separately replaceable relative to the fluid manifold.

In an embodiment, the fluid manifold is a single fluid manifold for each of a plurality of involved process fluids, such as blood, purified water, liquid concentrate and dialysis fluid. In an alternative embodiment, separate fluid manifolds may be provided for separate fluids, e.g., one for blood, purified water, another for liquid concentrate, and a fourth for dialysis fluid. In this manner, the separate fluid manifolds may be replaced individually as needed, e.g., the dialysis fluid manifold more often than the purified water manifold or the liquid concentrate.

In an embodiment, the pump and valve engine is a single pump and valve engine for each of a plurality of involved process fluids, such as blood, purified water, liquid concentrate and dialysis fluid. In an alternative embodiment, separate pump and valve engines may be provided for separate fluids, e.g., one for blood, purified water, another for liquid concentrate, and a fourth for dialysis fluid. In this manner, the separate pump and valve engines may be replaced individually as needed, e.g., the pump and valve engine that has the most pumping and valve chambers more often than the pump and valve engines having less pump and valve chambers.

In an embodiment, the pneumatic manifold is a single pneumatic manifold for each of a plurality of involved process fluids, such as blood, purified water, liquid concentrate and dialysis fluid. The single pneumatic manifold may be used with a single fluid manifold and/or a single pump and valve engine. The single pneumatic manifold may be used alternatively with multiple fluid manifolds and/or a multiple pump and valve engines. In an alternative embodiment, separate pneumatic manifolds may be provided for separate fluids, e.g., one for blood, purified another for liquid concentrate, and a fourth for dialysis fluid. The separate pneumatic manifolds are used in an embodiment with separate fluid manifolds and separate pump and valve engines. Here, the separate modular assemblies (each including a pneumatic manifold, pump and valve engine, and fluid manifold) may be located at different, convenient parts of the overall medical fluid or dialysis machine.

In a further alternative embodiment, a single modular assembly may include multiple fluid manifolds, multiple pump and valve engines and multiple pneumatic manifolds. For example, two fluid manifolds may be abutted against each other. Two pneumatic manifolds may then be located on the outsides of the modular assembly, sandwiching two pump and valve assemblies between the inner fluid manifolds and the outer pneumatic manifolds. In another implementation, two pneumatic manifolds may be abutted against each other. Two fluid manifolds may then be located on the outsides of the modular assembly, sandwiching two pump and valve assemblies between the inner pneumatic manifolds and the outer fluid manifolds.

The modular assemblies disclosed herein may be used to pump different fluids at once. Examples above have included dialysis fluid (fresh and used), water and liquid concentrate. In another example, the modular assemblies may alternatively or additionally pump blood. In one implementation, a blood set having both pump and valve engine and blood manifold structure is sealed to one side of a pneumatic manifold. That side of the manifold may be located at a front surface of the corresponding machine, so that a patient or user may removeably position the blood set against the front of the machine and into sealing engagement with the pneumatic manifold. The blood set may be held in place at the front of the machine via releaseable spring clamps.

The modular assemblies of the present disclosure may be clamped and held sealingly and releaseably together via bolts, clamps or combinations thereof. The rigid portions of the pump and valve engines and the fluid manifolds may have metal insets, both to countersinkingly receive the heads of the bolts and to provide female threads for receiving the male threaded ends of the bolts to prevent cracking. The machined metal pneumatic manifold may have recesses for countersinking the heads of the bolts and/or female threads for receiving the male threaded ends of the bolts. Fluid and pneumatic passageways, pump chambers, valve chambers and other components of the pump and valve engine are located and routed so as not to intersect with the bolts. Exterior clamps may be clamps that travel with the assembly and/or clamps that use a portion of the chassis of the machine to provide a compressive, clamping force.

As discussed in detail below, the pump and valve engines in alternative embodiments are removed partially or fully from any of the implementations discussed herein.

In light of the disclosure herein and without limiting the disclosure in any way, in a first aspect of the present disclosure, which may be combined with any other aspect listed herein unless specified otherwise, a medical fluid management assembly includes: (i) a pneumatic manifold including a plurality of pneumatic passageways and a plurality of pneumatic connectors; (ii) a pump and valve engine including a plurality of valve chambers and at least one pump chamber, the pump and valve engine including a plurality of pneumatic connectors mated sealingly and releaseably with the pneumatic connectors of the pneumatic manifold, the pump and valve engine further including a plurality of fluid connectors; and (iii) a fluid manifold including a plurality of fluid pathways and a plurality of fluid connectors mated sealingly and releaseably with the fluid connectors of the pump and valve engine.

In a second aspect of the present disclosure, which may be combined with any other aspect listed herein unless specified otherwise, the pneumatic manifold further includes at least one pneumatic source connector for connecting with at least one source of pneumatic pressure.

In a third aspect of the present disclosure, which may be combined with any other aspect listed herein unless specified otherwise, the fluid manifold includes at least one inlet/outlet connector for connecting to fluid tubing.

In a fourth aspect of the present disclosure, which may be combined with any other aspect listed herein unless specified otherwise, the plurality of pneumatic connectors of the pump and valve engine are ports that mate with the plurality of pneumatic connectors of the pneumatic manifold, which include recesses.

In a fifth aspect of the present disclosure, which may be combined with the fourth aspect in combination with any other aspect listed herein unless specified otherwise, the pneumatic manifold provides o-ring seals that extend around or within the recesses to seal against the ports of the pump and valve engine.

In a sixth aspect of the present disclosure, which may be combined with any other aspect listed herein unless specified otherwise, the plurality of fluid connectors of the pump and valve engine are ports that mate with the plurality of fluid connectors of the fluid manifold, which include recesses.

In a seventh aspect of the present disclosure, which may be combined with the sixth aspect in combination with any other aspect listed herein unless specified otherwise, the fluid manifold provides o-ring seals that extend around or within the recesses to seal against the ports of the pump and valve engine.

In an eighth aspect of the present disclosure, which may be combined with any other aspect listed herein unless specified otherwise, the pneumatic manifold includes a plurality of plates mated together, at least one of the plates defining grooves forming the pneumatic passageways.

In a ninth aspect of the present disclosure, which may be combined with any other aspect listed herein unless specified otherwise, the pump and valve engine includes first and second rigid plates at least partially separated by at least one flexible membrane.

In a tenth aspect of the present disclosure, which may be combined with the ninth aspect in combination with any other aspect listed herein unless specified otherwise, the first and second rigid plates are separated at areas defining pump and valve chambers by the at least one flexible membrane.

In an eleventh aspect of the present disclosure, which may be combined with the tenth aspect in combination with any other aspect listed herein unless specified otherwise, the first and second rigid plates further define at least one of a balance chamber, a water accumulation chamber, a mixing chamber, a water dearation chamber or a dialysis fluid dearation chamber.

In a twelfth aspect of the present disclosure, which may be combined with any other aspect listed herein unless specified otherwise, the fluid manifold includes at least one rigid plate forming the plurality of fluid pathways.

In a thirteenth aspect of the present disclosure, which may be combined with any other aspect listed herein unless specified otherwise, the fluid manifold includes multiple rigid plates sealed together to form the plurality of fluid pathways.

In a fourteenth aspect of the present disclosure, which may be combined with any other aspect listed herein unless specified otherwise, the medical fluid management assembly includes a plurality of pneumatic manifolds each including a plurality of pneumatic connectors mated sealingly and releaseably with the pneumatic connectors of the pump and valve engine.

In a fifteenth aspect of the present disclosure, which may be combined with any other aspect listed herein unless specified otherwise, the medical fluid management assembly includes a plurality of fluid manifolds each including a plurality of fluid connectors mated sealingly and releaseably with the fluid connectors of the pump and valve engine.

In a sixteenth aspect of the present disclosure, which may be combined with any other aspect listed herein unless specified otherwise, the medical fluid management assembly includes a plurality of pump and valve engines each including a plurality of pneumatic connectors mated sealingly and releaseably with the pneumatic connectors of the pneumatic manifold.

In a seventeenth aspect of the present disclosure, which may be combined with any other aspect listed herein unless specified otherwise, the medical fluid management assembly includes a plurality of pump and valve engines each including a plurality of fluid connectors mated sealingly and releaseably with the fluid connectors of the fluid manifold.

In an eighteenth aspect of the present disclosure, which may be combined with any other aspect listed herein unless specified otherwise, the pneumatic manifold is a first pneumatic manifold and the pump and valve engine is a first pump and valve engine, and which includes a second pneumatic manifold including a plurality of pneumatic connectors and a second pump and valve engine including a plurality of fluid connectors and a plurality of pneumatic connectors mated to the pneumatic connectors of the second pneumatic manifold.

In a nineteenth aspect of the present disclosure, which may be combined with the eighteenth aspect in combination with any other aspect listed herein unless specified otherwise, the fluid connectors of the second pump and valve engine are mated to fluid connectors of the fluid manifold.

In a twentieth aspect of the present disclosure, which may be combined with the eighteenth aspect in combination with any other aspect listed herein unless specified otherwise, the fluid manifold is a first fluid manifold and which incudes a second fluid manifold including a plurality of fluid connectors, and wherein the fluid connectors of the second pump and valve engine are mated to the fluid connectors of the second fluid manifold.

In a twenty-first aspect of the present disclosure, which may be combined with any other aspect listed herein unless specified otherwise, the fluid manifold is a first fluid manifold and the pump and valve engine is a first pump and valve engine, and which includes a second fluid manifold including a plurality of fluid connectors and a second pump and valve engine including a plurality of pneumatic connectors and a plurality of fluid connectors mated to the fluid connectors of the second fluid manifold.

In a twenty-second aspect of the present disclosure, which may be combined with the twenty-first aspect in combination with any other aspect listed herein unless specified otherwise, the pneumatic connectors of the pump and valve engine are mated to pneumatic connectors of the pneumatic plate.

In a twenty-third aspect of the present disclosure, which may be combined with any other aspect listed herein unless specified otherwise, the medical fluid management assembly includes at least one pneumatic valve attached to the pneumatic plate.

In a twenty-fourth aspect of the present disclosure, which may be combined with any other aspect listed herein unless specified otherwise, the medical fluid management assembly includes a fluid pumping cassette removeably attached to the pneumatic plate.

In a twenty-fifth aspect of the present disclosure, which may be combined with any other aspect listed herein unless specified otherwise, a medical fluid machine includes: (i) a source of pneumatic pressure; (ii) a purified water line; (iii) a liquid concentrate line; (iv) a to—extracorporeal circuit fresh dialysis fluid line; (v) a from—extracorporeal circuit used dialysis fluid line; (vi) a drain line; and (vii) a medical fluid management assembly including (a) a pneumatic manifold in pneumatic communication with the source of pneumatic pressure, the pneumatic manifold including a plurality of pneumatic passageways and a plurality of pneumatic connectors, (b) a pump and valve engine including a plurality of valve chambers and at least one pump chamber, the pump and valve engine including a plurality of pneumatic connectors mated sealingly and releaseably with the pneumatic connectors of the pneumatic manifold, the pump and valve engine further including a plurality of fluid connectors, and (c) a fluid manifold including a plurality of fluid pathways and a plurality of fluid connectors mated sealingly and releaseably with the fluid connectors of the pump and valve engine, the fluid manifold in fluid communication with at least one of the purified water line, the liquid concentrate line, the to—extracorporeal circuit fresh dialysis fluid line, the from—extracorporeal circuit used dialysis fluid line, or the drain line.

In a twenty-sixth aspect of the present disclosure, which may be combined with the twenty-fifth aspect in combination with any other aspect listed herein unless specified otherwise, the from—extracorporeal circuit used dialysis fluid line is a from—dialyzer line and, optionally, the to—extracorporeal circuit fresh dialysis fluid line is a to—dialyzer line.

In a twenty-seventh aspect of the present disclosure, which may be combined with the twenty-fifth aspect in combination with any other aspect listed herein unless specified otherwise, the fluid manifold is in fluid communication with each of the purified water line, the liquid concentrate line, the to—extracorporeal circuit fresh dialysis fluid line, the from—extracorporeal circuit used dialysis fluid line, and the drain line.

In a twenty-eighth aspect of the present disclosure, which may be combined with the twenty-fifth aspect in combination with any other aspect listed herein unless specified otherwise, the medical fluid machine includes a plurality of fluid manifolds, and wherein each of the purified water line, the liquid concentrate line, the to—extracorporeal circuit fresh dialysis fluid line, the from—extracorporeal circuit used dialysis fluid line, and the drain line are in fluid communication with one of the plurality of fluid manifolds.

In a twenty-ninth aspect of the present disclosure, which may be combined with the twenty-eighth aspect in combination with any other aspect listed herein unless specified otherwise, the fluid connectors of each of the fluid manifolds are mated with the fluid connectors of the pump and valve engine.

In a thirtieth aspect of the present disclosure, which may be combined with the twenty-eighth aspect in combination with any other aspect listed herein unless specified otherwise, the medical fluid machine includes a plurality of pump and valve engines each having a plurality of pneumatic connectors and a plurality of fluid connectors, and wherein the fluid connectors of each of the fluid manifolds are mated with the fluid connectors of one of the pump and valve engines.

In a thirty-first aspect of the present disclosure, which may be combined with the thirtieth aspect in combination with any other aspect listed herein unless specified otherwise, the pneumatic connectors of each of the pump and valve engines are mated with the pneumatic connectors of the pneumatic manifold.

In a thirty-second aspect of the present disclosure, which may be combined with the thirtieth aspect in combination with any other aspect listed herein unless specified otherwise, the medical fluid machine includes a plurality of pneumatic manifolds each having a plurality of pneumatic connectors, and wherein the pneumatic connectors of each of the pump and valve engines is mated with the pneumatic connectors of one of the pneumatic manifolds.

In a thirty-third aspect of the present disclosure, which may be combined with any other aspect listed herein unless specified otherwise, a medical fluid machine includes: (i) a first medical fluid management assembly located at a first portion of the machine, the first medical fluid management assembly including (a) a first pneumatic manifold including a plurality of pneumatic passageways and a plurality of pneumatic connectors, (b) a first pump and valve engine including a plurality of valve chambers and at least one pump chamber, the first pump and valve engine including a plurality of pneumatic connectors mated sealingly and releaseably with the pneumatic connectors of the first pneumatic manifold, the first pump and valve engine further including a plurality of fluid connectors, and (c) a first fluid manifold including a plurality of fluid pathways and a plurality of fluid connectors mated sealingly and releaseably with the fluid connectors of the first pump and valve engine; and (ii) a second medical fluid management assembly located at a second portion of the machine, the second medical fluid management assembly including (a) a second pneumatic manifold including a plurality of pneumatic passageways and a plurality of pneumatic connectors, (b) a second pump and valve engine including a plurality of valve chambers and at least one pump chamber, the second pump and valve engine including a plurality of pneumatic connectors mated sealingly and releaseably with the pneumatic connectors of the second pneumatic manifold, the second pump and valve engine further including a plurality of fluid connectors, and (c) a second fluid manifold including a plurality of fluid pathways and a plurality of fluid connectors mated sealingly and releaseably with the fluid connectors of the second pump and valve engine.

In a thirty-fourth aspect of the present disclosure, which may be combined with any other aspect listed herein unless specified otherwise, a medical fluid management assembly includes: (i) a pneumatic manifold including a plurality of plates sealed together to form a plurality of pneumatic passageways, a pneumatic valve chamber and a pneumatic pump chamber formed by at least one of the plates, the pneumatic valve chamber in pneumatic communication with at least one of the pneumatic passageways, and the pneumatic pump chamber in pneumatic communication with at least one of the pneumatic passageways; and (ii) a fluid manifold including a plurality of fluid pathways, a fluid valve chamber and a fluid pump chamber formed by the fluid manifold, the fluid valve chamber in selective fluid communication with the fluid pump chamber and at least one of the fluid pathways, wherein (a) the pneumatic valve chamber and the fluid valve chamber are mated together to compress at least one flexible valve chamber membrane or a valve chamber area of at least one common flexible membrane and (b) the pneumatic pump chamber and the fluid pump chamber are mated together to compress at least one flexible pump membrane or a pump chamber area of the at least one common flexible membrane, (iii) wherein at least one of (a) the pneumatic valve chamber extends from the at least one plate, (b) the pneumatic pump chamber extends from the at least one plate, (c) the fluid valve chamber extends from the manifold, or (d) the fluid pump chamber extends from the fluid manifold so as to aid in compressing their respective at least one flexible membrane or at least one flexible membrane area.

In a thirty-fifth aspect of the present disclosure, which may be combined with the thirty-fourth aspect in combination with any other aspect listed herein unless specified otherwise, wherein the plurality of pneumatic passageways are formed in at least one of the plates and are sealed via a gasket compressed between the plates.

In a thirty-sixth aspect of the present disclosure, which may be combined with the thirty-fourth aspect in combination with any other aspect listed herein unless specified otherwise, the fluid manifold includes a plurality of fluid plates, at least one of the fluid plates forming the plurality of fluid pathways, and wherein the fluid plates are sealed together to seal the fluid pathways.

In a thirty-seventh aspect of the present disclosure, which may be combined with the thirty-fourth aspect in combination with any other aspect listed herein unless specified otherwise, the medical fluid management assembly includes at least one electrically actuated pneumatic solenoid valve fixed to the pneumatic manifold and in selective pneumatic communication with at least one of the pneumatic passageways.

In a thirty-eighth aspect of the present disclosure, which may be combined with the thirty-fourth aspect in combination with any other aspect listed herein unless specified otherwise, the medical fluid management assembly includes at least one conductivity sensor having a conductive insert held by the fluid manifold, the insert positioned along one of the fluid pathways, the conductivity sensor further having a conductive conductivity probe held by the pneumatic manifold, the conductivity probe mated with the conductive insert.

In a thirty-ninth aspect of the present disclosure, which may be combined with the thirty-fourth aspect in combination with any other aspect listed herein unless specified otherwise, the pneumatic valve chamber and the fluid valve chamber are a first pneumatic valve chamber and fluid valve chamber, and which incudes a second pneumatic valve chamber and a second fluid valve chamber, the second fluid valve chamber in selective fluid communication with a first balancing chamber, the first balancing chamber separated from a second balancing chamber by at least one balancing chamber membrane or a balancing chamber area of the at least one common flexible membrane.

In a fortieth aspect of the present disclosure, which may be combined with the thirty-ninth aspect in combination with any other aspect listed herein unless specified otherwise, the first fluid valve chamber is in selective fluid communication with the second fluid valve chamber.

In a forty-first aspect of the present disclosure, which may be combined with the thirty-ninth aspect in combination with any other aspect listed herein unless specified otherwise, the first and second balancing chambers are provided as part of the fluid manifold.

In a forty-second aspect of the present disclosure, which may be combined with the thirty-fourth aspect in combination with any other aspect listed herein unless specified otherwise, the medical fluid management assembly includes a water accumulation chamber having at least one water accumulation chamber membrane or a water accumulation chamber area of the at least one common flexible membrane for expanding when more water fills the water accumulation chamber and contracting when less water fills the water accumulation chamber.

In a forty-third aspect of the present disclosure, which may be combined with the forty-second aspect in combination with any other aspect listed herein unless specified otherwise, the water accumulation chamber is in selective fluid communication with the fluid valve chamber.

In a forty-fourth aspect of the present disclosure, which may be combined with the forty-second aspect in combination with any other aspect listed herein unless specified otherwise, the water accumulation chamber is provided as part of the fluid manifold.

In a forty-fifth aspect of the present disclosure, which may be combined with the thirty-fourth aspect in combination with any other aspect listed herein unless specified otherwise, the medical fluid management assembly includes a mixing chamber having plural fluid inlets and a fluid outlet.

In a forty-sixth aspect of the present disclosure, which may be combined with the forty-fifth aspect in combination with any other aspect listed herein unless specified otherwise, the mixing chamber is in selective fluid communication with the fluid valve chamber.

In a forty-seventh aspect of the present disclosure, which may be combined with the forty-fifth aspect in combination with any other aspect listed herein unless specified otherwise, the mixing chamber is provided as part of the fluid manifold.

In a forty-eighth aspect of the present disclosure, which may be combined with the thirty-fourth aspect in combination with any other aspect listed herein unless specified otherwise, one of: (i) the pneumatic manifold is a first pneumatic manifold, and which includes a second pneumatic manifold operating with the fluid manifold or (ii) the fluid manifold is a first fluid manifold, and which includes a second fluid manifold operating with the pneumatic manifold.

In a forty-ninth aspect of the present disclosure, which may be combined with the thirty-fourth aspect in combination with any other aspect listed herein unless specified otherwise, the fluid manifold includes a purification filter in selective fluid communication with the fluid pump chamber.

In a fiftieth aspect of the present disclosure, which may be combined with any other aspect listed herein unless specified otherwise, a medical fluid management assembly includes: (i) a pneumatic manifold including a plurality of plates sealed together to form a plurality of pneumatic passageways, a first pneumatic valve chamber, a second pneumatic valve chamber, and a pneumatic pump chamber formed by at least one of the plates, the first pneumatic valve chamber in pneumatic communication with at least one of the pneumatic passageways, the second pneumatic valve chamber in pneumatic communication with at least one of the pneumatic passageways, and the pneumatic pump chamber in pneumatic communication with at least one of the pneumatic passageways; and (ii) a fluid manifold including a plurality of fluid pathways, a first fluid valve chamber, a second fluid valve chamber, a fluid pump chamber, a first balancing chamber and a second balancing chamber formed by the fluid manifold, the first fluid valve chamber in selective fluid communication with the fluid pump chamber and at least one of the fluid pathways, the second fluid valve chamber in selective fluid communication with the first balancing chamber and at least one of the fluid pathways, wherein (a) the first pneumatic valve chamber and the first fluid valve chamber are mated together to compress at least one first flexible valve chamber membrane or a first valve chamber area of at least one common flexible membrane, (b) the second pneumatic valve chamber and the second fluid valve chamber are mated together to compress at least one second flexible valve chamber membrane or a second valve chamber area of the at least one common flexible membrane, (c) the pneumatic pump chamber and the fluid pump chamber are mated together to compress at least one flexible pump membrane or a pump chamber area of the at least one common flexible membrane, and (d) the first balancing chamber and the second balancing chamber are mated together to compress at least one balancing chamber membrane or a balancing chamber area of the at least one common flexible membrane.

In a fifty-first aspect of the present disclosure, which may be combined with the fiftieth aspect in combination with any other aspect listed herein unless specified otherwise, the medical fluid management assembly includes a third pneumatic valve chamber and a third fluid valve chamber mated together to compress at least one third flexible valve chamber membrane or a third valve chamber area of the at least one common flexible membrane, the third fluid valve chamber in selective fluid communication with the second balancing chamber.

In a fifty-second aspect of the present disclosure, which may be combined with the fifty-first aspect in combination with any other aspect listed herein unless specified otherwise, the first fluid valve chamber is in selective fluid communication with (i) the second fluid valve chamber and (ii) the third fluid valve chamber.

In a fifty-third aspect of the present disclosure, which may be combined with the fifty-first aspect in combination with any other aspect listed herein unless specified otherwise, the medical fluid management assembly includes (i) a fourth pneumatic valve chamber and a fourth fluid valve chamber mated together to compress at least one fourth flexible valve chamber membrane or a fourth valve chamber area of the at least one common flexible membrane, the fourth fluid valve chamber in selective fluid communication with the first balancing chamber and (ii) a fifth pneumatic valve chamber and a fifth fluid valve chamber mated together to compress at least one fifth flexible valve chamber membrane or a fifth valve chamber area of the at least one common flexible membrane, the fifth fluid valve chamber in selective fluid communication with the second balancing chamber.

In a fifty-fourth aspect of the present disclosure, which may be combined with any other aspect listed herein unless specified otherwise, a medical fluid system includes: (i) a first medical fluid management assembly including (a) a first pneumatic manifold having a plurality of plates sealed together to form a plurality of pneumatic passageways, a pneumatic valve chamber and a pneumatic pump chamber formed by at least one of the plates, the pneumatic valve chamber in pneumatic communication with at least one of the pneumatic passageways, and the pneumatic pump chamber in pneumatic communication with at least one of the pneumatic passageways, and (b) a first fluid manifold having a plurality of fluid pathways, a fluid valve chamber and a fluid pump chamber formed by the fluid manifold, the fluid valve chamber in selective fluid communication with the fluid pump chamber and at least one of the fluid pathways, wherein (c) the pneumatic valve chamber and the fluid valve chamber are mated together to compress at least one flexible valve chamber membrane or a valve chamber area of at least one common flexible membrane and (d) the pneumatic pump chamber and the fluid pump chamber are mated together to compress at least one flexible pump membrane or a pump chamber area of the at least one common flexible membrane; and (ii) a second medical fluid management assembly including (a) a second pneumatic manifold having a plurality of plates sealed together to form a plurality of pneumatic passageways, a pneumatic valve chamber and a pneumatic pump chamber formed by at least one of the plates, the pneumatic valve chamber in pneumatic communication with at least one of the pneumatic passageways, and the pneumatic pump chamber in pneumatic communication with at least one of the pneumatic passageways, and (b) a second fluid manifold having a plurality of fluid pathways, a fluid valve chamber and a fluid pump chamber formed by the fluid manifold, the fluid valve chamber in selective fluid communication with the fluid pump chamber and at least one of the fluid pathways, wherein (c) the pneumatic valve chamber and the fluid valve chamber are mated together to compress at least one flexible valve chamber membrane or a valve chamber area of at least one common flexible membrane and (d) the pneumatic pump chamber and the fluid pump chamber are mated together to compress at least one flexible pump membrane or a pump chamber area of the at least one common flexible membrane.

In a fifty-fifth aspect of the present disclosure, which may be combined with the fifty-fourth aspect in combination with any other aspect listed herein unless specified otherwise, the first fluid manifold is a purified water manifold positioned and arranged to carry purified water and the second fluid manifold is a dialysis fluid manifold positioned and arranged to carry dialysis fluid.

In a fifty-sixth aspect of the present disclosure, which may be combined with the fifty-fifth aspect in combination with any other aspect listed herein unless specified otherwise, the purified water manifold is positioned adjacent to a concentrate source, while the dialysis fluid manifold is positioned adjacent to a dialysis fluid heater.

In a fifty-seventh aspect of the present disclosure, which may be combined with the fifty-fourth aspect in combination with any other aspect listed herein unless specified otherwise, the first fluid manifold is a dialysis fluid manifold positioned and arranged to carry dialysis fluid and the second fluid manifold is a blood manifold positioned and arranged to carry blood.

In a fifty-eighth aspect of the present disclosure, which may be combined with the fifty-seventh aspect in combination with any other aspect listed herein unless specified otherwise, the blood manifold is positioned adjacent to a dialyzer.

In a fifty-ninth aspect of the present disclosure, any of the structure and functionality disclosed in connection with FIGS. 1 to 19B may be combined with any of the other structure and functionality disclosed in connection with FIGS. 1 to 19B.

In light of the present disclosure and the above aspects, it is therefore an advantage of the present disclosure to provide an improved medical fluid management assembly, machine and method.

It is another advantage of the present disclosure to provide a medical fluid management assembly that is modular and scalable.

It is a further advantage of the present disclosure to provide a medical fluid management assembly that has a reduced number of components.

It is still another advantage of the present disclosure to provide a medical fluid management assembly that is relatively easy to use, maintain, assemble and test.

It is still a further advantage of the present disclosure to provide a medical fluid management assembly that is robust and may stand alone without need for the machine chassis.

It is yet another advantage of the present disclosure to provide a medical fluid management assembly that is flexible in terms of pneumatic and fluidic routing.

The advantages discussed herein may be found in one, or some, and perhaps not all of the embodiments disclosed herein. Additional features and advantages are described herein, and will be apparent from, the following Detailed Description and the figures.

BRIEF DESCRIPTION OF THE FIGURES

FIG. 17 is a schematic elevation view of a yet another embodiment for a medical fluid management assembly of the present disclosure, illustrating system modularity.

FIGS. 18A to 18C are schematic elevation views of a further embodiment for a medical fluid management assembly of the present disclosure, further illustrating system modularity.

DETAILED DESCRIPTION

System Hardware

The examples described herein are applicable to any medical fluid therapy system that delivers a medical fluid, such as blood, dialysis fluid, substitution fluid, purified or sterilized water, liquid concentrate, or an intravenous drug. The examples are particularly well suited for kidney failure therapies, such as all forms of peritoneal dialysis ("PD"), hemodialysis ("HD"), hemofiltration ("HF"), hemodiafiltration ("HDF") and continuous renal replacement therapies ("CRRT"), referred to herein collectively or generally individually as renal failure therapy. Moreover, the machines and any of the modular fluid management systems and methods described herein may be used in clinical or home settings. For example, the machine and the modular fluid management systems and methods may be employed in an in-center HD machine, which runs virtually continuously throughout the day. Alternatively, they may be used in a home HD machine, which can for example be run at night while the patient is sleeping. Moreover, each of the renal failure therapy examples described herein may include a diffusion membrane or filter, such as a dialyzer, e.g., for HD or HDF, or a hemofilter, e.g., for HF.

Figure 1:
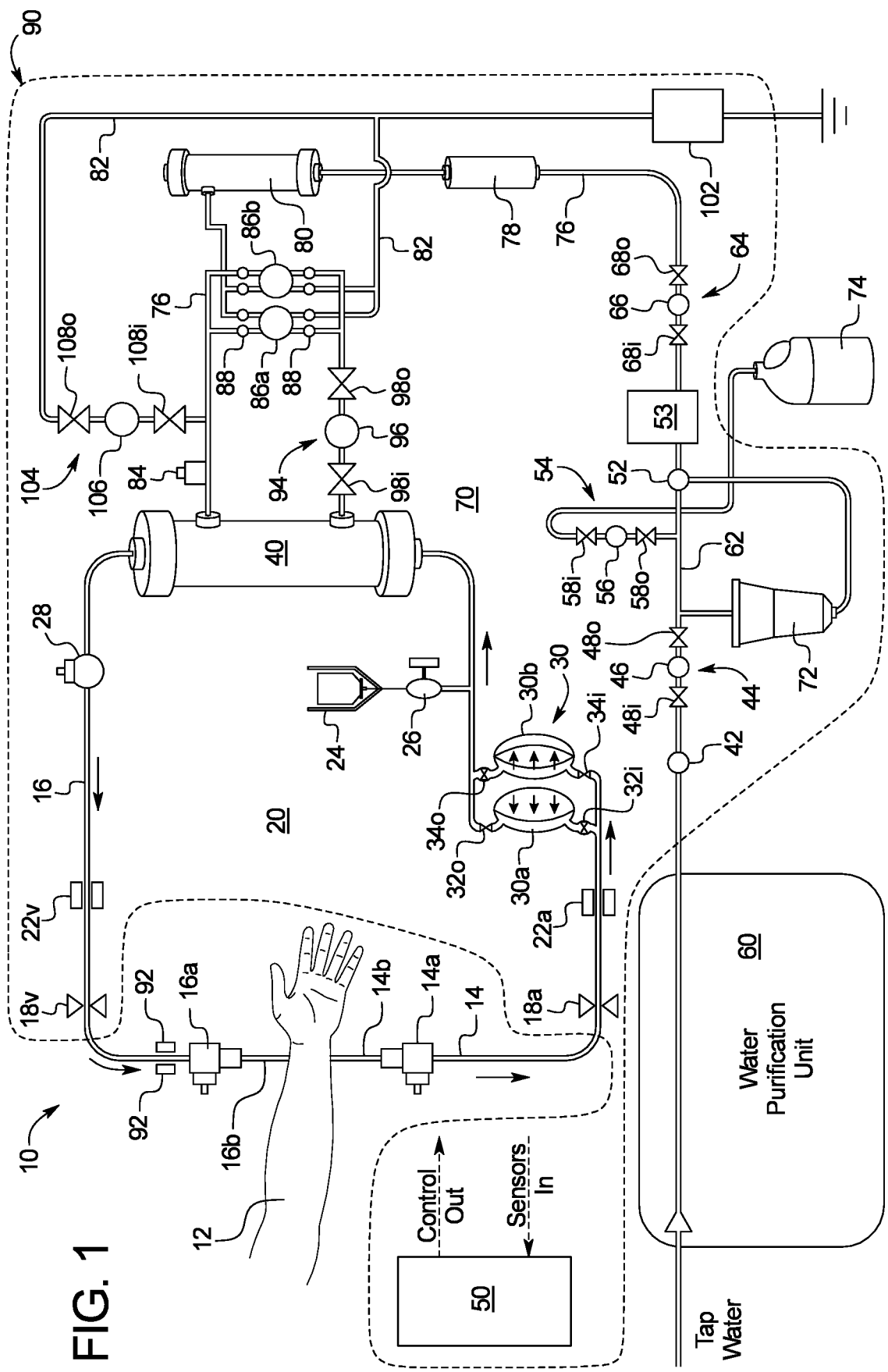
FIG. 1 is a schematic illustration of one embodiment of a renal failure therapy employing any of the modular fluid management systems and methods of the present disclosure.

Referring now to FIG. 1, one embodiment for a renal failure therapy system 10 employing any of the modular fluid management assemblies and methods described herein is illustrated using an HD machine 90. Generally, system 10 is shown having a simplified version of the dialysis fluid or process fluid delivery circuit. The blood circuit is also simplified. It should be appreciated that the circuits have been simplified to make the description of the present disclosure easier, and that the systems if implemented would have additional structure and functionality, such as is found in the publication incorporated by reference above.

System 10 of FIG. 1 includes a blood circuit 20. Blood circuit 20 pulls blood from and returns blood to a patient 12. Blood is pulled from patient 12 via an arterial line 14, and is returned to the patient via a venous line 16. Arterial line 14 includes an arterial line connector 14a that connects to an arterial needle 14b, which is in blood draw flow communication with patient 12. Venous line 16 includes a venous line connector 16a that connects to a venous needle 16b, which is in blood return flow communication with the patient. Arterial and venous lines 14 and 16 also include line clamps 18a and 18v, which can be spring-loaded, fail-safe mechanical pinch clamps. Line clamps 18a and 18v are closed automatically in an emergency situation in one embodiment.

Arterial and venous lines 14 and 16 also include air or bubble detectors 22a and 22v, respectively, which can be ultrasonic air detectors. Air or bubble detectors 20*a* and 20*v* look for air in the arterial and venous lines 14 and 16, respectively. If air is detected by one of air detectors 22*a* and 22*v*, system 10 closes line clamps 18*a* and 18*v*, pauses the blood and dialysis fluid pumps, and provides instructions to the patient to clear the air so that treatment can resume.

A blood pump 30 is located in arterial line 14 in the illustrated embodiment. In the illustrated embodiment, blood pump 30 includes a first blood pump chamber 30*a* and a second blood pump chamber 30*b*. Blood pump chamber 30*a* operates with an inlet valve 32*i* and an outlet valve 32*o*. Blood pump chamber 30*b* operates with an inlet valve 34*i* and an outlet valve 34*o*. In an embodiment, blood pump chambers 30*a* and 30*b* are each blood receptacles that include a hard outer shell, e.g., spherical, with a flexible diaphragm located within the shell, forming a diaphragm pump. One side of each diaphragm receives blood, while the other side of each diaphragm is operated by negative and positive air pressure (or is vented to atmosphere). Blood pump 30 is alternatively a peristaltic pump operating with the arterial line 14 tube.

A heparin vial 24 and heparin pump 26 are located between blood pump 30 and blood filter 40 (e.g., dialyzer) in the illustrated embodiment. Heparin pump 26 can be a pneumatic pump or a syringe pump (e.g., stepper motor driven syringe pump). Supplying heparin upstream of blood filter 40 helps to prevent clotting of the blood filter membranes.

A control unit 50 includes one or more processor and memory. Control unit 50 receives air detection signals from air detectors 22*a* and 22*v* (and other sensors of system 10, such as temperature sensors, blood leak detectors, conductivity sensors, pressure sensors, and access disconnection transducers 92), and controls components such as line clamps 18*a* and 18*v*, blood pump 30, heparin pump 26, and the dialysis fluid pumps.

Blood exiting blood filter 40 via venous line 16 flows through an airtrap 28. Airtrap 28 removes air from the blood before the dialyzed blood is returned to patient 12 via venous line 16 as discussed in detail below.

With the hemodialysis version of system 10 of FIG. 1, dialysis fluid is pumped along the outside of the membranes of blood filter 40, while blood is pumped through the insides of the blood filter membranes. Fresh dialysis fluid is prepared beginning with the purification of water via a water purification unit 60. One suitable water purification unit is set forth in U.S. Patent Publication No. 2011/0197971, entitled, "Water Purification System and Method", filed Apr. 25, 2011, the entire contents of which are incorporated herein by reference and relied upon. In one embodiment, water purification unit includes filters and other structure to purify tap water (e.g., remove pathogens and ions such as chlorine) so that the water is in one implementation below 0.03 endotoxin units/ml ("EU/ml") and below 0.1 colony forming units/ml ("CFU/ml"). Water purification unit 60 can be provided in a housing separate from the housing of the hemodialysis machine, which includes blood circuit 20 and a dialysis fluid circuit 70.

In the illustrated embodiment, dialysis fluid circuit 70 includes a water accumulation chamber 42. Purified water from purification unit 60 is stored in a water accumulation chamber 42. Water accumulation chamber 42 provides a surplus of water for water pump 44 when demand for purified water increases for whatever reason.

In one embodiment, purified water from water purification unit 60 is pumped along water line 62 though water accumulation chamber 42 and bicarbonate cartridge 72. Acid from container 74 is pumped along an acid line into a mixing chamber 52 with bicarbonated water flowing from bicarbonate cartridge 72 to form an electrolytically and physiologically compatible dialysis fluid solution. The pumps and temperature-compensated conductivity sensors used to properly mix the purified water with the bicarbonate and acid are discussed next.

Dialysis fluid circuit 70 provides a to—blood filter or fresh dialysis fluid pump 64. Fresh dialysis fluid pump 64 is in one embodiment configured the same a blood pump 30. Fresh dialysis fluid pump 64, like pump 30, includes a pair of pump chambers (shown as one pump chamber 66, which again may be spherically configured), each operating with inlet and outlet valve chambers 68*i* and 68*o*, respectively. Pump chambers 66, like with blood pump 30, are operated alternatingly so that one pump chamber 66 is filling with HD dialysis fluid, while the other pump chamber 66 is expelling HD dialysis fluid.

Pump 64 is a to—blood filter dialysis fluid pump. In one embodiment, a second dual chamber pump 94, like pump 64, is located in or in front of drain line 82 to push used dialysis fluid to drain. Used dialysis fluid pump 94 includes dual chambers 96 (only one illustrated) operating with inlet and outlet valve chambers 98*i* and 98*o*, respectively.

A third chamber pump 44 is provided for pumping pump purified water from water accumulation chamber 42 and through a bicarbonate cartridge 72. Purified water pump 44 may also include two pump chambers 46 (only one illustrated) each operating with inlet and outlet valve chambers 48*i* and 48*o*, respectively.

A fourth chamber pump 54 is provided to pump acid from acid container 74 into an acid line. Acid pump 54 may include a pump chamber 56 operating with inlet and outlet valve chambers 58*i* and 58*o*, respectively. Acid pump 54 may have only a single pump chamber 56 because continuous pumping is not as important in the acid line due at least in part to a buffering dialysis fluid tank 53 provided between a mixing chamber 52 and to—blood filter dialysis fluid pump 64 in one embodiment.

A fifth pod pump 104 provided in drain line 82 is used to remove a known amount of ultrafiltration ("UF") when the HD therapy is provided. UF pump 104 includes a pump chamber 106 operating with inlet and outlet valve chambers 108*i* and 108*o*, respectively. System 10 controls and tracks UF pump 104 to control and know how much ultrafiltrate has been removed from the patient. System 10 ensures that the necessary amount of ultrafiltrate is removed from the patient by the end of treatment.

Any on or more of the above-described pumps may alternatively be a peristaltic pump operating with a tube.

FIG. 1 also illustrates that dialysis fluid is pumped along a fresh dialysis fluid line 76, through a heater 78 and an ultrafilter 80, before reaching blood filter 40, after which the used dialysis fluid is pumped to drain via drain line 82. Heater 78 heats the dialysis fluid to body temperature or about 37° C. Ultrafilter 80 further cleans and purifies the dialysis fluid before reaching blood filter 40, filtering bugs or contaminants introduced for example via bicarbonate cartridge 72 or acid container 74 from the dialysis fluid.

Dialysis fluid circuit 70 also includes a sample port 84 in the illustrated embodiment. Dialysis fluid circuit 70 may further include a blood leak detector (not illustrated but used to detect if a blood filter 40 fiber is torn).

In the illustrated embodiment, fluid balancing to an from dialyzer 40 is performed via balance chambers 86*a* and 86*b* and corresponding valves 88. The valves are sequenced such that used dialysis fluid fills one of the balance chambers 86*a* and 86b, pushing a like amount of fresh dialysis fluid to dialyzer 40, while fresh dialysis fluid fills the other of the balance chambers 86a and 86b, pushing a like amount of used dialysis fluid to drain line 82. The roles of the two balance chambers 86a and 86b are then reversed to maintain a relatively constant flow of fresh fluid to dialyzer 40 and used fluid to drain line 82. Balance chambers 86a and 86b ensure to a large extent that the amount of fresh fluid to dialyzer 40 and the amount of used fluid to drain line 82 are equal. UF pump 104 is placed in a parallel drain line (not illustrated) leading from dialyzer 40. It uses a smaller, more accurate pump chamber in one embodiment to meter precise amounts of UF from patient 12.

In the illustrated embodiment, hemodialysis system 10 is an online, pass-through system that pumps dialysis fluid through blood filter one time and then pumps the used dialysis fluid to drain. Both blood circuit 20 and dialysis fluid circuit 70 may be hot water disinfected after each treatment, such that blood circuit 20 and dialysis fluid circuit 70 may be reused. In one implementation, blood circuit 20 including blood filter 40 is hot water disinfected and reused daily for about one month, while dialysis fluid circuit 70 is hot water disinfected and reused for about six months. To perform the disinfection and other procedures, such as priming, arterial line 14 and venous line 16 are both connected in one embodiment to a drain cassette 102 located in drain line 82. When arterial line 14 and venous line 16 are plugged into drain cassette 102, water for disinfection, and dialysis fluid for priming, may be circulated throughout blood circuit 20 and dialysis fluid circuit 70 on both sides of dialyzer 40 for complete disinfection or priming.

In alternative embodiments, or for CRRT for example, multiple bags of sterilized dialysis fluid or infusate are ganged together and used one after another. In such a case, the emptied supply bags can serve as drain or spent fluid bags. In other alternative embodiments, substitution fluid from the balance chambers 86a and 86b may flow directly to arterial line 14 and/or venous line 16 of extracorporeal circuit 20 instead of to dialyzer 40.

A machine 90 of system 10 includes an enclosure as indicated by the dotted line of FIG. 1. The enclosure of machine 90 varies depending upon the type of treatment, whether the treatment is in-center or a home treatment, and whether the dialysis fluid/infusate supply is a batch-type (e.g., bagged) or on-line. Although not illustrated in FIG. 1, the front of the enclosure of machine 90 may have structures configured to releaseably clamp airtrap 28.

Figure 2:
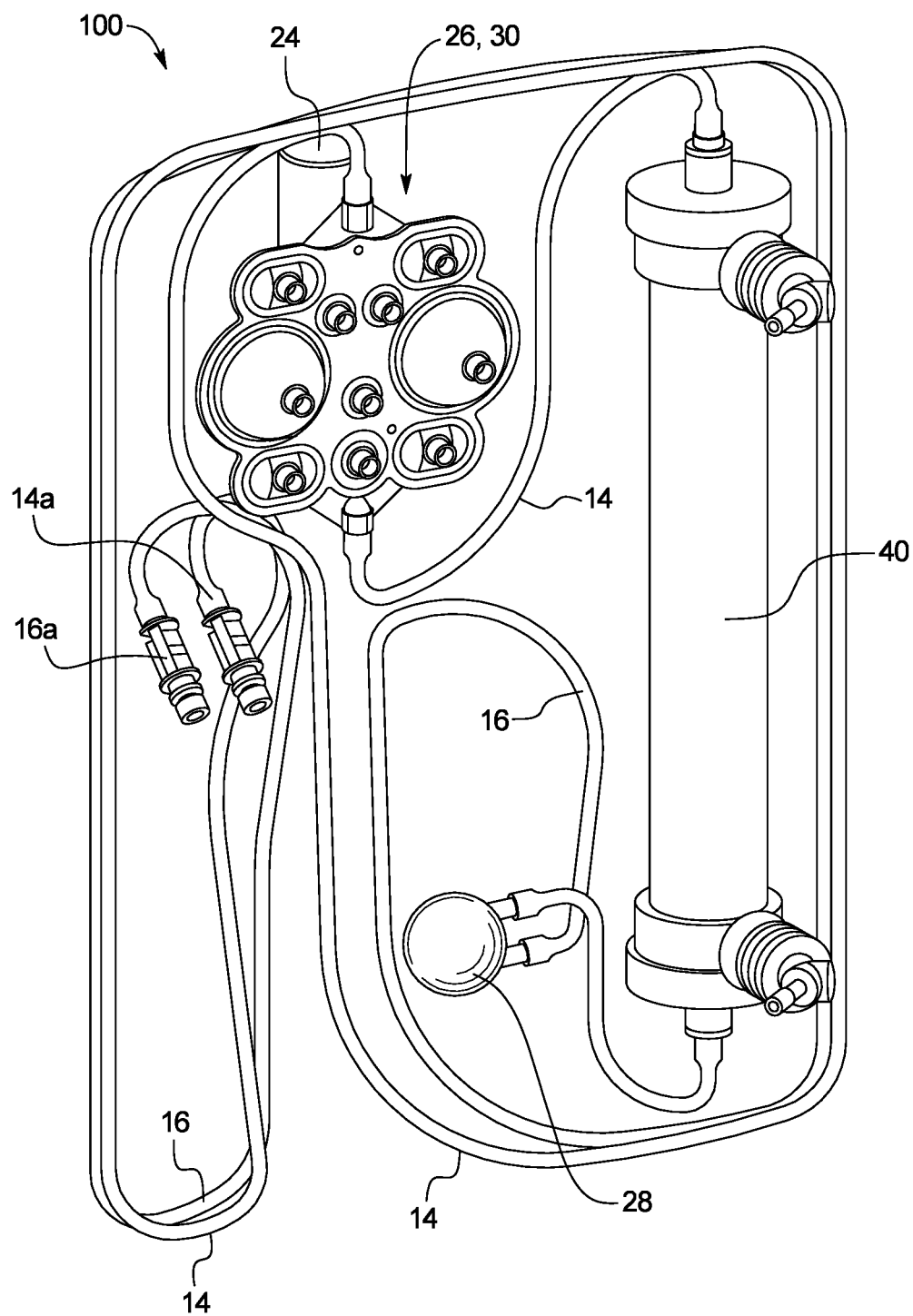
FIG. 2 is a perspective view of one embodiment for a blood set of the present disclosure.

FIG. 2 further illustrates that machine 90 of system 10 of FIG. 1 may operate with a blood set 100. Blood set 100 includes arterial line 14, venous line 16, heparin vial 24 and heparin pump 26/blood pump 30, blood filter 40 (e.g., dialyzer), and airtrap 28. Airtrap 28 may be located in venous line 16 to remove air from the blood before being returned to patient 12. Alternatively or additionally, one or more airtrap 28 may be located in water line 62, fresh dialysis fluid line 76, and/or anywhere in dialysis fluid circuit 70, to improve mixing accuracy and/or to remove air from fresh dialysis fluid line before reaching filter or dialyzer 40. In an embodiment, to a large extent, dialysis fluid circuit components 70 may be located inside machine 90, while blood set 100 may be mounted to the outside of the machine Reviewing FIG. 1 again, the primary purified water components for machine 90 of system 10 include water accumulation chamber 42 and water pump 44. The primary mixing components for machine 90 of system 10 include bicarbonate cartridge 72, mixing chamber 52 (note that acid container 74 is not held by machine 90 but could be in an alternative embodiment). The primary dialysis fluid components for machine 90 of system 10 include dialysis fluid holding tank 53, fresh dialysis fluid pump 64, heater 78, ultrafilter 80, balance chambers 86a and 86b and used dialysis fluid pump 94. The primary blood transfer components of blood set 100 include dialyzer 40, airtrap 28, and blood pump/heparin pump 30/26.

It is contemplated in one embodiment to provide a single medical fluid management assembly housing all of the purified water components, mixing components and dialysis fluid components, and to operate blood set 100 separately as it is illustrated in FIG. 2. In an alternative embodiment, a single medical fluid management assembly is provided for all of the purified water components, mixing components, dialysis fluid components, and for operating blood set 100. In another alternative embodiment, a first medical fluid management assembly is provided for the purified water components and mixing components, and a second medical fluid management assembly is provided for the dialysis fluid components, while blood set 100 is operated separately as it is illustrated in FIG. 2. In a further alternative embodiment, a first medical fluid management assembly is provided for the purified water components and mixing components, and a second medical fluid management assembly is provided for the dialysis fluid components, while blood set 100 is operated with one of the first or second medical fluid management assemblies. In still another alternative embodiment, a first medical fluid management assembly is provided for the purified water components, a second medical fluid management assembly is provided for the mixing components, and a third medical fluid management assembly is provided for the dialysis fluid components, while blood set 100 is operated separately as it is illustrated in FIG. 2. In yet a further alternative embodiment, a first medical fluid management assembly is provided for the purified water components, a second medical fluid management assembly is provided for the mixing components, and a third medical fluid management assembly is provided for the dialysis fluid components, but blood set 100 is operated with one of the first, second or third medical fluid management assemblies. In any of the embodiments described above where a separate medical fluid management assembly is provided for the dialysis fluid components, that medical fluid management assembly may still further alternatively be split into separate fresh dialysis fluid and used fluid assemblies.

In an embodiment, each of the pumps is a pneumatically actuated pump that operates with a inlet valve and an outlet valve. In particular, purified water pump 44 operates with inlet and outlet valve chambers 48i and 48o, Acid pump 54 operates with inlet and outlet valve chambers 58i and 58o. Fresh dialysis fluid pump 64, operates with inlet and outlet valve chambers 68i and 68o. Used dialysis fluid pump 94 operates with inlet and outlet valve chambers 98i and 98o. Blood pump 30 operates with inlet and outlet valve chambers 32i/34i, 32o, 34o. The UF pump is not illustrated may operates the same way in one embodiment.

Each of the above pumps may have the same sized pump chamber 46, 56, 66, 96, 106, and 30a, 30b, respectively. Alternatively, any of the pump chambers 46, 56, 66, 96, 106, and 30a, 30b may be sized differently. For example, the pump chambers for the liquid acid pump 44 and the UF pump 104 may be smaller than the others. Regardless, each of the pumps 44, 54, 64, 94, 30 and 104 pump may be provided as found in any of FIGS. 3 to 5. That is, each of pumps 44, 54, 64, 94, 30 and 104 may have any of the structure, function and any of the alternatives discussed in connection with any of FIGS. 3 to 5. For each pump, the inlet valve is opened, the outlet valve is closed, while negative pressure is applied to the pump membrane to draw fluid into the pump. The inlet valve is closed, the outlet valve is opened, while positive pressure is applied to the pump membrane to expel fluid from the pump.

Any of water line 62, concentrate lines, dialysis fluid line 76, used dialysis fluid or drain line 82, arterial blood line 14 and/or venous blood line may include pneumatic valves provided in addition to the inlet and outlet valves associated with pumps 44, 54, 64, 94, 30 and 104. For example, balance chambers 86a and 86b include corresponding valves 88. Any of those additional valves may have any of the structure, function and any of the alternatives discussed in connection with the pneumatically actuated valves of FIGS. 3 to 5.

Other primary components for machine 90 of system 10 are not pneumatically actuated including, water accumulation chamber 42, bicarbonate cartridge 72, mixing chamber 52, dialysis fluid holding tank 53, heater 78, ultrafilter 80, balance chambers 86a and 86b, dialyzer 40, and airtrap 28. Of those components, it is contemplated that bicarbonate cartridge 72, dialysis fluid holding tank 53 and heater are provided with machine 90 but outside of, but in fluid communication with, the one or more medical fluid management assembly of system 10. Ultrafilter 80 may or may not be provided with the one or more medical fluid management assembly as discussed in more detail below.

Figure 3:
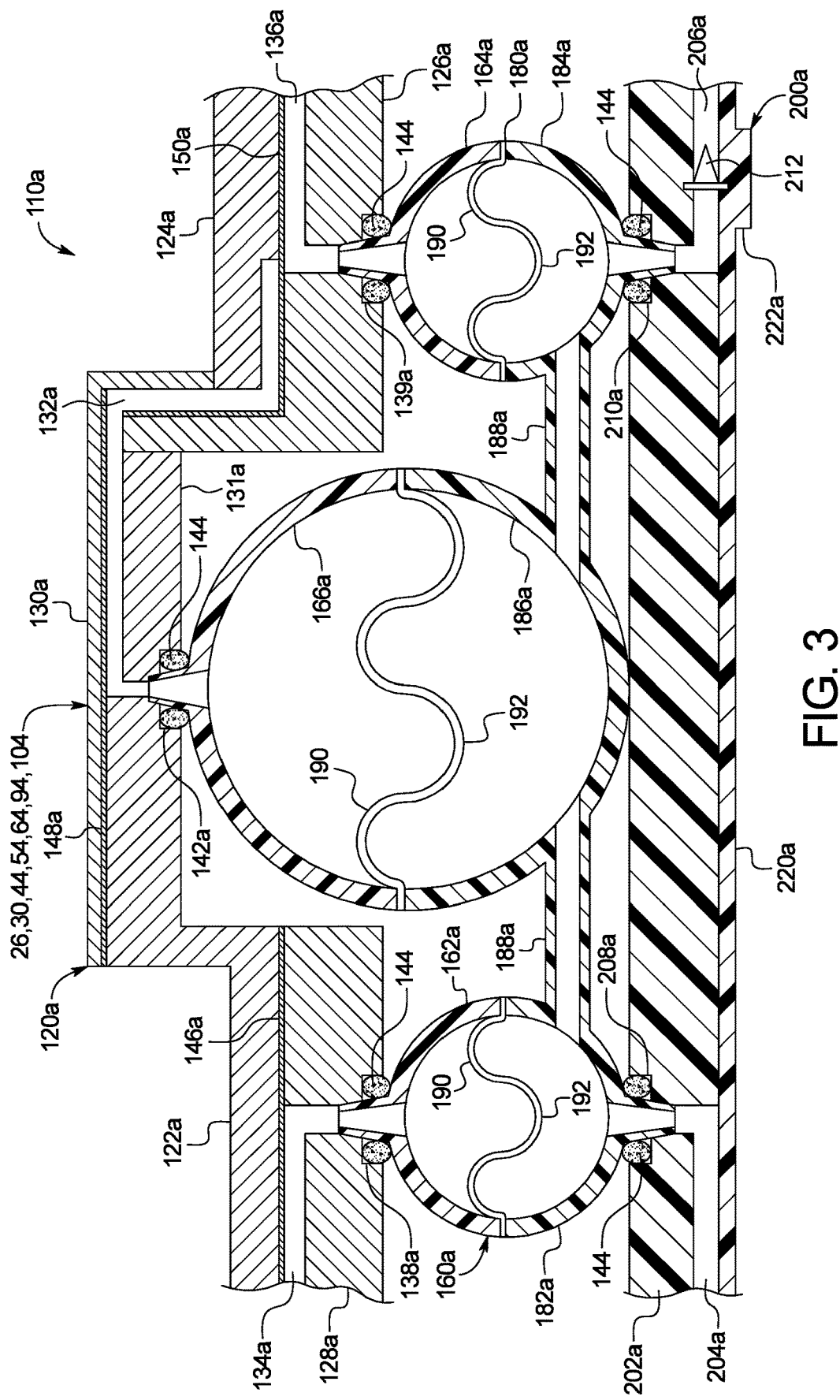
FIG. 3 is a side sectioned view of a pneumatically actuated water, dialysis fluid, liquid concentrate, blood or other medical fluid pump for one embodiment of a medical fluid management assembly of the present disclosure.

Referring now to FIG. 3, a cross-sectional view of a pump portion 26, 30, 44, 54, 64, 94 and 104 of one embodiment of a medical fluid management assembly 110a of the present disclosure is illustrated. Medical fluid management assembly 110a in the illustrated embodiment includes three primary components, namely, a pneumatic manifold 120a, a pump and valve engine 160a, and a fluid manifold 200a.

Pneumatic manifold 120a in an embodiment includes metal plates or pieces 122a, 124a, 126a, 128a, and 130a, which may be machined aluminum, steel, stainless steel and combinations thereof. Plates or pieces 122a, 124a, 126a, 128a, and 130a may alternatively be made of a plastic material, such as molded plastic. Where abutted, plates or pieces 122a, 124a, 126a, 128a, and 130a may be bolted removeably together using bolts and nuts and/or female mating threads.

Plates or pieces 122a and 124a collectively define a pneumatic pumping groove 132a for carrying positive and negative pressure (or vent to atmosphere) selectively to a pneumatic pump chamber of pumps 26, 30, 44, 54, 64, 94 and 104. Plate 128a defines a pneumatic inlet valve groove 134a for carrying positive and negative pressure (or vent to atmosphere) selectively to an inlet pneumatic valve chamber of pumps 26, 30, 44, 54, 64, 94 and 104. Piece 126a defines a pneumatic outlet valve groove 136a for carrying positive and negative pressure (or vent to atmosphere) selectively to an outlet pneumatic valve chamber of pumps 26, 30, 44, 54, 64, 94 and 104.

Plate 128a defines an inlet valve o-ring seat 138a for sealingly holding an inlet valve o-ring 144. Piece 126a defines an outlet valve o-ring seat 139a for sealingly holding an outlet valve o-ring 144. Piece 122a defines a pump chamber o-ring seat 142a for sealingly holding a pump chamber o-ring 144.

A gasket 146a is compressed between piece 122a and plate 128a to seal pneumatic grooves or passageways formed in piece 122a and/or plate 128a, e.g., groove or passageway 134a. A gasket 148a is compressed between piece 122a and plate 120a to seal pneumatic grooves or passageways formed in piece 122a and/or plate 120a, e.g., groove or passageway 132a. A gasket 150a is compressed between piece 124a and piece 126a to seal pneumatic grooves or passageways formed in piece 124a and/or piece 126a, e.g., grooves or passageways 132a and 136a. Gaskets 146a, 148a and 150a may be compressible silicone for example. Gaskets 146a, 148a and 150a may be individual gaskets or be made provided as part of a common flexible sheet or membrane forming other gaskets or gasketed areas.

Pneumatic grooves or passageways lead to electrically actuated pneumatic solenoid valves (not illustrated), which may be spring closed when non-energized and opened when energized. The electrically actuated pneumatic solenoid valves selectively allow, under electrical control by control unit 50 (FIG. 1), positive on/off pressure, negative on/off pressure, positive variable pressure, and/or positive variable pressure (or vent to atmosphere) to reach a pneumatic inlet valve chamber, a pneumatic outlet valve chamber or a pneumatic pump chamber. The electrically actuated pneumatic solenoid valves may be mounted to pneumatic manifold 120a.

Pump and valve engine 160a for pump portion 26, 30, 44, 54, 64, 94 and 104 of one embodiment of a medical fluid management assembly 110a includes pneumatic caps 162a, 164a and 166a and a fluid piece 180a. Caps 162a, 164a, 166a and piece 180a may each be made of a rigid, medically safe plastic, such as, polyethylene ("PE"), polypropylene ("PP"), polyvinyl chloride ("PVC"), polysulfone, polystyrene, polycarbonate ("PC"), acrylic, cyclo-olefin copolymers ("COCs"), acrylonitrile butadiene styrene ("ABS"), polyolefin and the like. In general, metal cross-sections are shown herein as having a uniform hatch, while plastic cross-sections are shown herein as having a thin/thick line hatch. Materials contacting blood or dialysis are biocompatible and disinfected or sterilized as needed.

Pneumatic caps 162a, 164a and 166a form a pneumatic inlet valve chamber, a pneumatic outlet valve chamber and a pneumatic pump chamber, respectively, for pump portion 26, 30, 44, 54, 64, 94 and 104 of one embodiment of a medical fluid management assembly 110a. Pneumatic caps 162a, 164a and 166a each define a pneumatic port as illustrated that fits sealingly within a respective o-ring 144 and abuts against a mating groove or passageway, e.g., groove 134a, groove 136a and groove 132a, to provide an airtight connection between pump and valve engine 160a and pneumatic manifold 120a.

Fluid piece 180a in the illustrated embodiment provides mating fluid chambers 182a, 184a and 186a. Fluid inlet valve chamber 182a mates with pneumatic inlet valve cap 162a. Fluid outlet valve chamber 184a mates with pneumatic outlet valve cap 164a. Fluid pump chamber 186a mates with pneumatic pump cap 166a. Fluid inlet valve chamber 182a, fluid outlet valve chamber 184a and fluid pump chamber 186a each define a fluid port as illustrated that fits sealingly within a respective o-ring 144 and abuts against a mating fluid pathway of fluid manifold 200a to provide an fluid-tight connection between pump and valve engine 160a and fluid manifold 200a.

Fluid piece 180a in the illustrated embodiment is formed with fluid tube sections 188a, namely, a first fluid tube section 188a linking fluid inlet valve chamber 182a and fluid pump chamber 186a and a second fluid tube section 188a linking fluid pump chamber 186a and fluid outlet valve chamber 184a. Fluid inlet valve chamber 182a, fluid outlet valve chamber 184a, fluid pump chamber 186a and fluid tube sections 188a are molded as a single structure in one embodiment. There may be two sizes, for example, a larger size for blood pump 30, water pump 44, dialysis fluid pumps 64 and 94 and a smaller size for heparin pump 26, acid pump 54, and UF pump 104. Three or more different sizes may be provided alternatively, e.g., a third even smaller size for heparin pump 26.

It should be appreciated that while the pump and valve chambers for ease of illustration are shown being spherical, any or all of the pump and valve chambers could have an alternative shape, such as an elliptical or oblong shape.

One or more flexible membrane or sheeting 190, 192 is located between pneumatic caps 162a, 164a and 166a and fluid piece 180a. Membranes or sheeting 190, 192 may be made of polyvinyl chloride ("PVC"), polyethylene, kraton or polyolefin, for example, or of another medically safe flexible plastic or rubber. Membranes or sheeting 190, 192 may be flat and caused to stretch during actuation or be preformed or predomed to have a shape the same as or similar to pneumatic caps 162a, 164a and 166a and/or fluid inlet valve chamber 182a, fluid outlet valve chamber 184a, and fluid pump chamber 186a, so that membranes or sheeting 190, 192 do not stretch and instead flap back and forth.

It is important to prevent fluid from leaking into pneumatic manifold 120a. It is accordingly contemplated to provide two or more plies or sheets 190, 192 in case one tears, has a pinhole, becomes misaligned, etc. Additionally, it is contemplated to pressure check each membrane 190, 192 before each treatment by applying pneumatic positive pressure inside pneumatic caps 162a, 164a and 166a, isolating the pneumatic lines leading from pneumatic caps 162a, 164a and 166a, and monitoring the pressures in the isolated areas to look for pressure decays. In this manner, leaking membranes or sheeting 190, 192 may be detected before medical fluid is introduced into fluid piece 180a.

To catch fluid leaks occurring during treatment, it is contemplated to provide any one or more of (i) electrical contact sensors formed in an insulating housing (not illustrated) in pneumatic grooves or passageways 132a, 134a, 136a, wherein the presence of a conductive liquid such as dialysis fluid or blood completes a circuit, which is sensed, (ii) a capacitive or inductive sensor (not illustrated) in pneumatic grooves or passageways 132a, 134a, 136a, wherein the presence of a liquid such as water, dialysis fluid or blood changes an electrical field, which is sensed, or (iii) a memory storing a known pressure spike that occurs when a non-leaking membrane 190, 192 closes against pneumatic caps 162a, 164a and 166a, wherein a deviation of that pressure spike is sensed when a leak or misalignment of membrane 190, 192 occurs.

One or more membrane 190, 192 is placed under positive pneumatic pressure at pneumatic cap 162a to close against fluid inlet valve chamber 182a to close the inlet valve. One or more membrane 190, 192 is placed under negative pneumatic pressure or is vented to atmosphere at pneumatic cap 162a to open fluid inlet valve chamber 182a (or allow it to be opened). One or more membrane 190, 192 is placed under positive pneumatic pressure at pneumatic cap 164a to close against fluid outlet valve chamber 184a to close the outlet valve. One or more membrane 190, 192 is placed under negative pneumatic pressure or is vented to atmosphere at pneumatic cap 164a to open fluid outlet valve chamber 184a (or allow it to be opened).

One or more membrane 190, 192 is placed under positive pneumatic pressure at pneumatic cap 166a to close against fluid pump chamber 186a to cause a pump-out stroke (with inlet valve chamber closed and outlet valve chamber open). One or more membrane 190, 192 is placed under negative pneumatic pressure at pneumatic cap 166a to open fluid pump chamber 186a to cause a pump-in stroke (with inlet valve chamber open and outlet valve chamber closed).

Fluid manifold 200a for pump portion 26, 30, 44, 54, 64, 94 and 104 of one embodiment of a medical fluid management assembly 110a includes a fluid pathway plate 202a heat sealed, sonically sealed, or solvent bonded to a cover plate 220a. Plates 202a and 220a may each be made of a rigid, medically safe plastic, such as, polyethylene ("PE"), polypropylene ("PP"), polyvinyl chloride ("PVC"), polysulfone, polystyrene, polycarbonate ("PC"), acrylic, cycloolefin copolymers ("COCs"), acrylonitrile butadiene styrene ("ABS"), polyolefin and the like.

Fluid pathway plate 202a includes or defines a fluid inlet pathway 204a and a fluid outlet pathway 206a. Fluid pathway plate 202a further defines an inlet valve o-ring seat 208a for sealingly holding an inlet valve o-ring 144. Fluid pathway plate 202a further defines an outlet valve o-ring seat 210a for sealingly holding an outlet valve o-ring 144. Any fluid pathway discussed herein, such as fluid outlet pathway 206a, may be fitted with a one-way valve or check valve 212. Fluid flows from left to right in FIG. 3. One-way valve or check valve 212 prevents fluid from backflowing from right to left into fluid pump chamber 186a.

Cover plate 220a is permanently sealed to fluid pathway plate 202a in one embodiment, so that separate gasketing is not needed to seal fluid inlet pathway 204a or fluid outlet pathway 206a. Cover plate 220a may include a raised or buttressed section 222a to help hold and seal check valve 212 in place. In the illustrated embodiment, fluid inlet valve chamber 182a and fluid outlet valve chamber 184a each define a fluid port that fits sealingly within a respective o-ring 144 and abuts against a mating fluid pathway, e.g., fluid inlet pathway 204a and a fluid outlet pathway 206a, to provide a fluid-tight connection between pump and valve engine 160a and fluid manifold 200a.

Fluid, such as water, liquid concentrate, dialysis fluid or blood flows under negative pressure from fluid inlet pathway 204a, into inlet valve chamber 182a, through first fluid tube section 188a, into fluid pump chamber 186a, and under positive pressure from fluid pump chamber 186a, through second fluid tube section 188a and outlet valve chamber 184a, and out fluid inlet pathway 206a to a desired destination. For fluid pumping benefitting from continuous flow, or almost continuous flow, such as for blood pump 30, water pump 44, and dialysis fluid pumps 64 and 94, the structure just described for FIG. 3 is doubled, so that as one fluid pump chamber 186a fills with blood, water or dialysis fluid, the other fluid pump chamber 186a may expel blood, water or dialysis fluid. Certain pumping, such as for heparin pump 26, acid pump 54 and UF pump 104, does not require continuous pumping, so that the single fluid pump chamber 186a and other structure of FIG. 3 will suffice.

Figure 4:
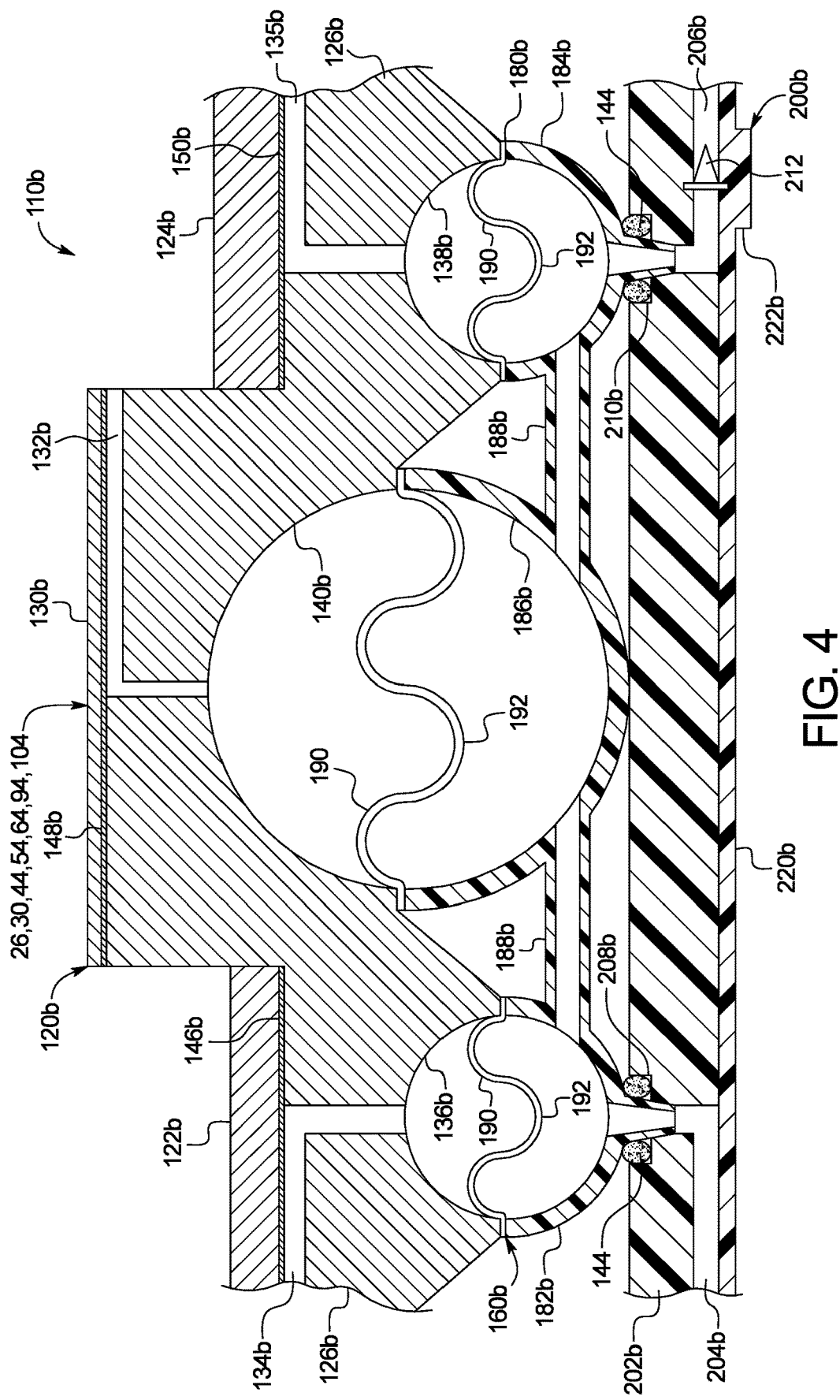
FIG. 4 is a side sectioned view of a pneumatically actuated water, dialysis fluid, liquid concentrate, blood or other medical fluid pump for another embodiment of a medical fluid management assembly of the present disclosure.

Referring now to FIG. 4, a cross-sectional view of a pump portion 26, 30, 44, 54, 64, 94 and 104 of another embodiment of a medical fluid management assembly 110b of the present disclosure is illustrated. Medical fluid management assembly 110b in the illustrated embodiment again includes three primary components, namely, a pneumatic manifold 120b, a pump and valve engine 160b, and a fluid manifold 200b.

Pneumatic manifold 120b in an embodiment includes metal plates or pieces 122b, 124b, and 126b. Notably, metal plate or piece 126b is significantly larger than piece 126a of FIG. 3 and eliminates and thereby serves the purpose of the upper half of pump and valve engine 160a in FIG. 3. Metal plates or pieces 122b, 124b, and 126b may again be machined aluminum, steel, stainless steel and combinations thereof. Where abutted, plates or pieces 122b, 124b and 126b may be bolted removeably together using bolts and nuts and/or female mating threads.

Plate 126b defines pneumatic pumping groove 132b for carrying positive and negative pressure (or vent to atmosphere) selectively to a pneumatic pump chamber of pumps 26, 30, 44, 54, 64, 94 and 104. Plate 126b also defines a pneumatic inlet valve groove 134b for carrying positive and negative pressure (or vent to atmosphere) selectively to an inlet pneumatic valve chamber of pumps 26, 30, 44, 54, 64, 94 and 104. Plate 126b further defines a pneumatic outlet valve groove 136b for carrying positive and negative pressure (or vent to atmosphere) selectively to an outlet pneumatic valve chamber of pumps 26, 30, 44, 54, 64, 94 and 104.

Pneumatic manifold 120b eliminates the need for upper o-rings seats and associated o-rings 144. As with FIG. 3, a gasket 146b is compressed between plate 122b and plate 126b to seal pneumatic grooves or passageways formed in piece 122b and/or plate 126b, e.g., groove or passageway 134b. A gasket 148b is compressed between plate 130b and plate 126b to seal pneumatic grooves or passageways formed in plate 130b and/or plate 126b, e.g., groove or passageway 132b. A gasket 150b is compressed between plate 124b and plate 126b to seal pneumatic grooves or passageways formed in plate 124b and/or plate 126b, e.g., groove or passageway 136b. Gaskets 146b, 148b and 150b may again be compressible silicone for example. Pneumatic grooves or passageways lead to electrically actuated pneumatic solenoid valves as described above with FIG. 3, which may be spring closed when non-energized and opened when energized.

Pump and valve engine 160b for pump portion 26, 30, 44, 54, 64, 94 and 104 of one embodiment of a medical fluid management assembly 110b has eliminated pneumatic caps 162a, 164a and 166a but still provides fluid piece 180b. Fluid piece 180b may again be made of a rigid, medically safe plastic, such as, polyethylene ("PE"), polypropylene ("PP"), polyvinyl chloride ("PVC"), polysulfone, polystyrene, polycarbonate ("PC"), acrylic, cyclo-olefin copolymers ("COCs"), acrylonitrile butadiene styrene ("ABS"), polyolefin and the like.

Pneumatic caps 162a, 164a and 166a in FIG. 3 have been replaced respectively by a pneumatic inlet valve chamber 136b, a pneumatic outlet valve chamber 138b and a pneumatic pump chamber 140b for pump portion 26, 30, 44, 54, 64, 94 and 104 of medical fluid management assembly 110b. Advantageously, sealing with o-rings 144 has been eliminated.

Fluid piece 180b in the illustrated embodiment is the same (including all alternatives) as fluid piece 180a in FIG. 3 and provides mating fluid chambers 182b, 184b and 186b. Fluid inlet valve chamber 182b mates with pneumatic inlet valve chamber 136b. Fluid outlet valve chamber 184b mates with pneumatic outlet valve chamber 138b. Fluid pump chamber 186a mates with pneumatic pump chamber 140b. Fluid inlet valve chamber 182b, fluid outlet valve chamber 184b and fluid pump chamber 186b each define a fluid port as illustrated that fits sealingly within a respective o-ring 144 and abuts against a mating fluid pathway of fluid manifold 200b to provide an fluid-tight connection between pump and valve engine 160b and fluid manifold 200b.

Fluid piece 180b like before is formed in an embodiment with fluid tube sections 188b, namely, a first fluid tube section 188b linking fluid inlet valve chamber 182b and fluid pump chamber 186b and a second fluid tube section 188b linking fluid pump chamber 186b and fluid outlet valve chamber 184b. Fluid inlet valve chamber 182b, fluid outlet valve chamber 184b, fluid pump chamber 186b and fluid tube sections 188b are molded as a single structure and sized as needed in one embodiment. It should again be appreciated that while the pump and valve chambers for ease of illustration are shown being spherical, any or all of the pump and valve chambers could have an alternative shape, such as an elliptical or oblong shape.

One or more flexible membrane or sheeting 190, 192 is located between pneumatic chambers 136b, 138b and 140b and fluid piece 180b. Membranes or sheeting 190, 192 may be made of polyvinyl chloride ("PVC"), polyethylene, kraton or polyolefin, for example, or of another medically safe flexible plastic or rubber and have any of the alternatives discussed above in FIG. 3. Moreover, any one or more of (i) pressure checks, (ii) electrical contact sensors, (ii) capacitive or inductive sensors, or (iii) a memory storing a known pressure spike that occurs when a non-leaking membrane 190, 192 may again be used to prevent leaking fluid from entering pneumatic manifold 120b. Pneumatic pumping operates the same as described in FIG. 3.

Fluid manifold 200b for pump portion 26, 30, 44, 54, 64, 94 and 104 of for one embodiment of medical fluid management assembly 110b is the same as above (including all alternatives) and includes a fluid pathway plate 202b heat sealed, sonically sealed, or solvent bonded to a cover plate 220b. Plates 202b and 220b may each be made of a rigid, medically safe plastic, such as, polyethylene ("PE"), polypropylene ("PP"), polyvinyl chloride ("PVC"), polysulfone, polystyrene, polycarbonate ("PC"), acrylic, cyclo-olefin copolymers ("COCs"), acrylonitrile butadiene styrene ("ABS"), polyolefin and the like.

Fluid pathway plate 202b includes or defines a fluid inlet pathway 204b and a fluid outlet pathway 206b. Fluid pathway plate 202b further defines an inlet valve o-ring seat 208b for sealingly holding an inlet valve o-ring 144. Fluid pathway plate 202b further defines an outlet valve o-ring seat 210b for sealingly holding an outlet valve o-ring 144. Any fluid pathway discussed herein may again be fitted with a one-way valve or check valve 212.

Cover plate 220b is permanently sealed to fluid pathway plate 202b in one embodiment, so that separate gasketing is not needed. Cover plate 220b may again include a raised or buttressed section 222b to help hold and seal check valve 212 in place. Fluid inlet valve chamber 182b and fluid outlet valve chamber 184b may each again define a pneumatic port that fits sealingly within a respective o-ring 144 and abuts against a mating fluid pathway to provide a fluid-tight connection between pump and valve engine 160a and fluid manifold 200a.

Again, for fluid pumping benefitting from continuous flow, or almost continuous flow, such as for blood pump 30, water pump 44, and dialysis fluid pumps 64 and 94, the structure just described for FIG. 4 is doubled, so that as one fluid pump chamber 186b fills with blood, water or dialysis fluid, the other fluid pump chamber 186b may expel blood, water or dialysis fluid. Certain pumping, such as for heparin pump 26, acid pump 54 and UF pump 104, does not require continuous pumping, so that the single fluid pump chamber 186b and other structure of FIG. 4 will suffice.

Figure 5:
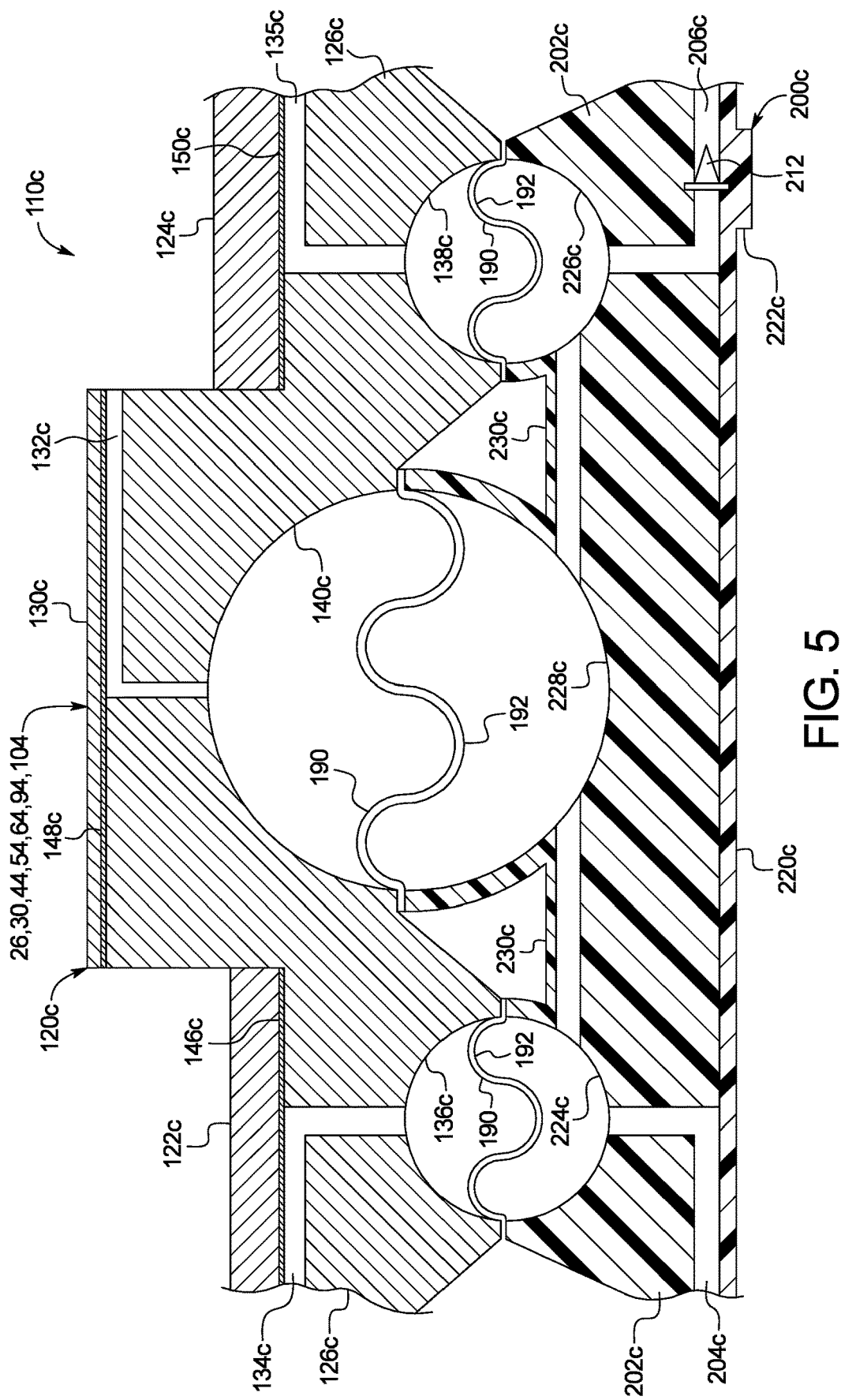
FIG. 5 is a side sectioned view of a pneumatically actuated water, dialysis fluid, liquid concentrate, blood or other medical fluid pump for a further embodiment of a medical fluid management assembly of the present disclosure.

Referring now to FIG. 5, a cross-sectional view of a pump portion 26, 30, 44, 54, 64, 94 and 104 of another embodiment of a medical fluid management assembly 110c of the present disclosure is illustrated. Medical fluid management assembly 110c in the illustrated embodiment includes two primary components, namely, a pneumatic manifold 120c and a fluid manifold 200c, wherein the pump and valve engine has been eliminated.

Pneumatic manifold 120c is the same as pneumatic manifold 120b of FIG. 4 (including all alternatives) in an embodiment and includes metal plates or pieces 122c, 124c, and 126c, which may again be machined aluminum, steel, stainless steel and combinations thereof. Where abutted, plates or pieces 122c, 124c and 126c may be bolted removeably together using bolts and nuts and/or female mating threads.

Plate 126c defines pneumatic pumping groove 132c for carrying positive and negative pressure (or vent to atmosphere) selectively to a pneumatic pump chamber of pumps 26, 30, 44, 54, 64, 94 and 104. Plate 126c also defines a pneumatic inlet valve groove 134c for carrying positive and negative pressure (or vent to atmosphere) selectively to an inlet pneumatic valve chamber of pumps 26, 30, 44, 54, 64, 94 and 104. Plate 126c further defines a pneumatic outlet valve groove 136b for carrying positive and negative pressure (or vent to atmosphere) selectively to an outlet pneumatic valve chamber of pumps 26, 30, 44, 54, 64, 94 and 104.

Gasket 146c is compressed between plate 122c and plate 126c to seal pneumatic grooves or passageways formed in piece 122c and/or plate 126c, e.g., groove or pathway 134c. Gasket 148c is compressed between plate 130c and plate 126c to seal pneumatic grooves or passageways formed in plate 130c and/or plate 126c, e.g., groove or passageway 132c. Gasket 150c is compressed between plate 124c and plate 126c to seal pneumatic grooves or passageways formed in plate 124c and/or plate 126c, e.g., groove or passageway 135c. Gaskets 146c, 148c and 150c may again be compressible silicone for example. Pneumatic grooves or passageways lead to electrically actuated pneumatic solenoid valves as described above with FIG. 3, which may be spring closed when non-energized and opened when energized.

Pump and valve engines 160a and 160b have been eliminated completely. Pneumatic caps 162a, 164a and 166a in FIG. 3 have again been replaced respectively by a pneumatic inlet valve chamber 136c, a pneumatic outlet valve chamber 138c and a pneumatic pump chamber 140c of pneumatic manifold 120c, eliminating sealing with o-rings 144 for airtight connection. Fluid piece 180b in FIG. 4 has also been eliminated completely in FIG. 5.

Fluid inlet valve chamber 182b of FIG. 4 has been replaced by fluid inlet valve chamber 224c of fluid manifold 200c, which mates with pneumatic inlet valve chamber 136b. Fluid outlet valve chamber 184b of FIG. 4 has been replaced by fluid outlet valve chamber 226c of fluid manifold 200c, which mates with pneumatic outlet valve chamber 138b. Fluid pump chamber 186a of FIG. 4 has been replaced by fluid pump chamber 228c of fluid manifold 200c. Fluid inlet valve chamber 224c, fluid outlet valve chamber 226c and fluid pump chamber 228c as illustrated are each formed in fluid pathway plate 202b, which eliminates separate fluid ports, o-ring seats and o-rings 144 in fluid manifold 200c.

Fluid pathway plate 202b forms fluid tube sections 230c, namely, a first fluid tube section 230c linking fluid inlet valve chamber 224c and fluid pump chamber 228c and a second fluid tube section 230c linking fluid pump chamber 228c and fluid outlet valve chamber 226c. Fluid inlet valve chamber 224c, fluid outlet valve chamber 226c, fluid pump chamber 228c and fluid tube sections 230c are molded as a single structure and sized as needed in one embodiment. It should again be appreciated that while the pump and valve chambers for ease of illustration are shown being spherical, any or all of the pump and valve chambers could have an alternative shape, such as an elliptical or oblong shape.

One or more flexible membrane or sheeting 190, 192 is located between pneumatic chambers 136c, 138c and 140c and fluid chambers 224c, 226c and 228c, respectively. Membranes or sheeting 190, 192 may again be made of polyvinyl chloride ("PVC"), polyethylene, kraton or polyolefin, for example, or of another medically safe flexible plastic or rubber and have any of the alternatives discussed above in FIG. 3. Moreover, any one or more of (i) pressure checks, (ii) electrical contact sensors, (ii) capacitive or inductive sensors, or (iii) a memory storing a known pressure spike that occurs when a non-leaking membrane 190, 192 may again be used to prevent leaking fluid from entering pneumatic manifold 120b. Pneumatic pumping operates the same as described in FIG. 3.

Fluid manifold 200c includes a cover plate 220c heat sealed, sonically sealed, or solvent bonded to fluid pathway plate 202c, so that separate gasketing is not needed. Plates 202c and 220c may each be made of a rigid, medically safe plastic, such as, polyethylene ("PE"), polypropylene ("PP"), polyvinyl chloride ("PVC"), polysulfone, polystyrene, polycarbonate ("PC"), acrylic, cyclo-olefin copolymers ("COCs"), acrylonitrile butadiene styrene ("ABS"), polyolefin and the like. Fluid pathway plate 202c includes or defines a fluid inlet pathway 204c leading to fluid inlet valve chamber 224c and a fluid outlet pathway 206c leading from fluid outlet valve chamber 226c. Any fluid pathway discussed herein may again be fitted with a one-way valve or check valve 212. Cover plate 220c may again include a raised or buttressed section 222c to help hold and seal check valve 212 in place.

Again, for fluid pumping benefitting from continuous flow, or almost continuous flow, such as for blood pump 30, water pump 44, and dialysis fluid pumps 64 and 94, the structure just described for FIG. 5 is doubled, so that as one fluid pump chamber 228c fills with blood, water or dialysis fluid, the other fluid pump chamber 228c may expel blood, water or dialysis fluid. Certain pumping, such as for heparin pump 26, acid pump 54 and UF pump 104, does not require continuous pumping, so that the single fluid pump chamber 228c and other structure of FIG. 5 will suffice.

Figure 6:
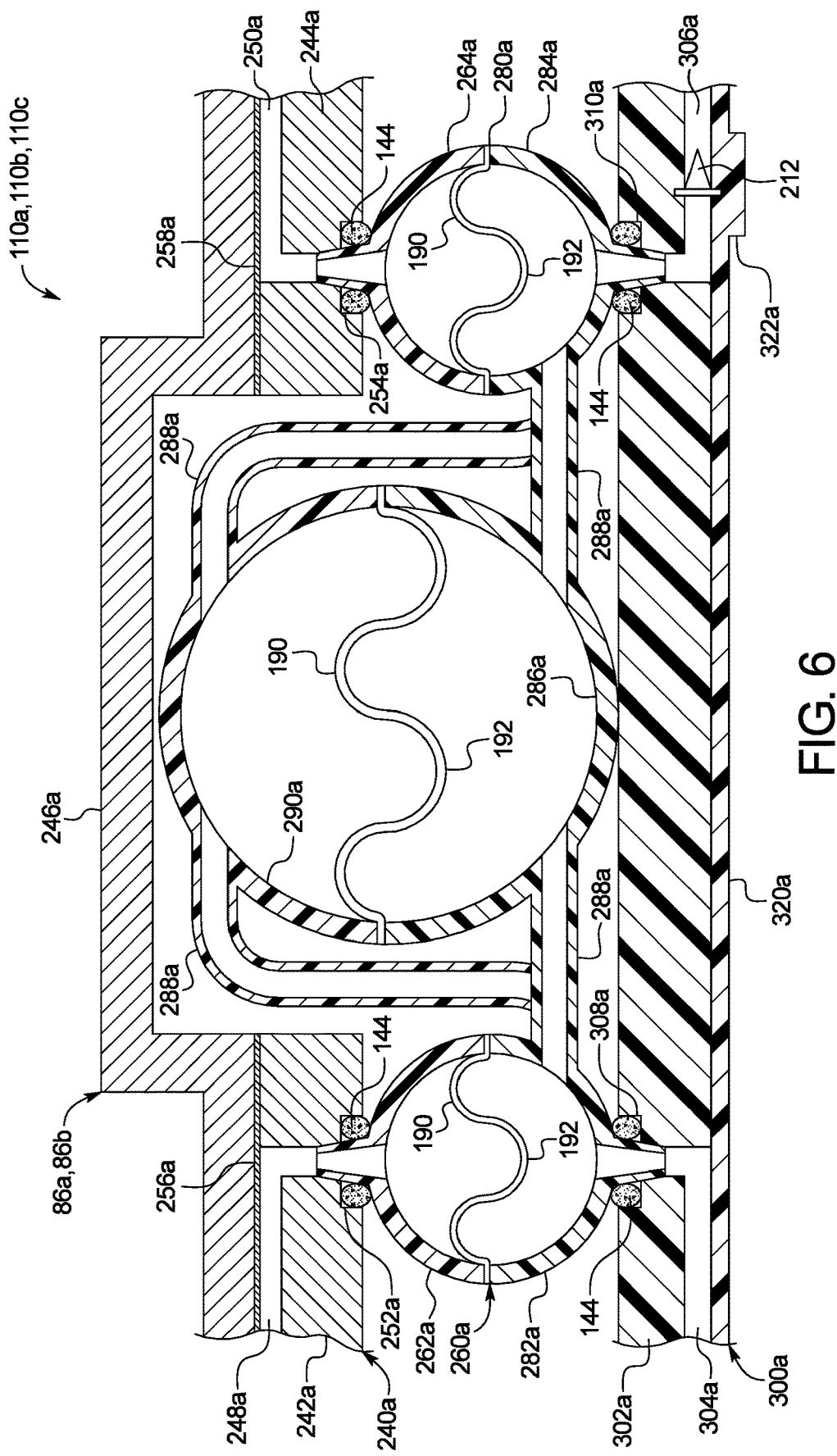
FIG. 6 is a side sectioned view of one embodiment for a balance chamber for any of the medical fluid management assemblies of the present disclosure.

Referring now to FIG. 6, a cross-sectional view of one embodiment of a balance chamber portion 86a, 86b for inclusion with any of fluid management assemblies 110a to 110c discussed above is illustrated. Balance chamber portion 86a, 86b of FIG. 6 in the illustrated embodiment includes three primary components, namely, a pneumatic manifold 240a, a valve engine 260a, and a fluid manifold 300a.

Pneumatic manifold 240a in an embodiment includes metal plates or pieces 242a, 244a and 246a, which may be machined aluminum, steel, stainless steel and combinations thereof. Where abutted, plates or pieces 242a, 244a and 246a may be bolted removeably together using bolts and nuts and/or female mating threads.

Plate 242a defines a pneumatic valve groove 248a for carrying positive and negative pressure (or vent to atmosphere) selectively to a pneumatic valve chamber of valve engine 260a of balance chamber 86a, 86b. Plate 244a defines a pneumatic valve groove 250a for carrying positive and negative pressure (or vent to atmosphere) selectively to a pneumatic valve chamber of valve engine 260a of balance chamber 86a, 86b. There is no pneumatic connection to the upper balancing chamber 290a of balance chamber 86a, 86b because upper balancing chamber 290a carries liquid.

Plate 242a defines a valve o-ring seat 252a for sealingly holding a valve o-ring 144. Plate 244a defines a valve o-ring seat 254a for sealingly holding an outlet valve o-ring 144.

A gasket 256a is compressed between plate 242a and plate 246a to seal pneumatic grooves or passageways formed in plate 242a and/or plate 246a, e.g., groove or passageway 248a. A gasket 258a is compressed between plate 244a and plate 246a to seal pneumatic grooves or passageways formed in plate 244a and/or plate 246a, e.g., groove or passageway 250a. Gaskets 256a and 258a may be compressible silicone for example. The pneumatic grooves or passageways lead to electrically actuated pneumatic solenoid valves (not illustrated) as discussed above, which may be spring closed when non-energized and opened when energized. The electrically actuated pneumatic solenoid valves may be mounted to pneumatic manifold 240a.

Valve engine 260a for balance chamber portion 86a, 86b of medical fluid management assembly 110a, 110b or 110c includes pneumatic caps 262a and 264a and a fluid piece 280a. Caps 262a, 264a and piece 280a may each be made of a rigid, medically safe plastic, such as, polyethylene ("PE"), polypropylene ("PP"), polyvinyl chloride ("PVC"), polysulfone, polystyrene, polycarbonate ("PC"), acrylic, cyclo-olefin copolymers ("COCs"), acrylonitrile butadiene styrene ("ABS"), polyolefin and the like.

Pneumatic caps 262a and 264a form a pneumatic first valve chamber and a pneumatic second valve chamber for pump portion balance chambers 86a, 86b. Pneumatic caps 262a and 264a each define a pneumatic port as illustrated that fits sealingly within a respective o-ring 144 and abuts against a mating groove or passageway, e.g., groove 248a and groove 250a, to provide an airtight connection between valve engine 260a and pneumatic manifold 240a.

Fluid piece 280a in the illustrated embodiment provides mating fluid chambers 282a, 284a and 286a. Fluid valve chamber 282a mates with pneumatic valve cap 262a. Fluid valve chamber 284a mates with pneumatic valve cap 264a. Fluid balancing chamber 286a mates with a second fluid balancing chamber 290 of a second fluid piece 280a, which is located behind the illustrated fluid piece 280a in FIG. 6. Fluid valve chamber 282a and fluid valve chamber 284a each define a fluid port as illustrated that fits sealingly within a respective o-ring 144 and abuts against a mating fluid pathway of fluid manifold 300a to provide an fluid-tight connection between valve engine 260a and fluid manifold 300a.

Fluid piece 280a in the illustrated embodiment is formed with two fluid tube sections 288a, namely, a first fluid tube section 288a linking fluid valve chamber 282a and lower fluid balancing chamber 286a and a second fluid tube section 288a linking lower fluid balancing chamber 286a and fluid valve chamber 284a. The second fluid piece 280a, located behind the fluid piece 280a visible in FIG. 6, also includes two fluid tube sections 288a, namely, a first fluid tube section 288a linking fluid valve chamber 282a (not visible in FIG. 6) and upper fluid balancing chamber 290a and a second fluid tube section 288a linking upper fluid balancing chamber 290a and fluid valve chamber 284a (not visible in FIG. 6).

The first and second fluid pieces 280a in FIG. 6 are formed as separate pieces in one embodiment, so that the fully visible fluid piece 280a with lower fluid balancing chamber 286a may be inserted into fluid manifold 300a before the partially hidden fluid piece 280a with upper fluid balancing chamber 290a is inserted into fluid manifold 300a, so that upper fluid balancing chamber 290a mates with lower fluid balancing chamber 286a. Fluid valve chamber 282a, fluid valve chamber 284a, fluid balancing chamber 286a or 290a and fluid tube sections 188a are molded as a single fluid piece 280a forming structure in one embodiment.

In an alternative embodiment, first and second fluid pieces 280a in FIG. 6 are formed or molded as a single piece. Here, upper fluid balancing chamber 290a is permanently sealed, e.g., sonically welded, heat sealed or solvent bonded, to lower fluid balancing chamber 286a, capturing flexible membranes 190, 192 between the balancing chambers. The four valves (two visible, two hidden in FIG. 6) connected balancing chambers 286a, 290a are then at once inserted sealingly into o-rings 144 of fluid manifold 300a.

It should again be appreciated that while the balancing and valve chambers for ease of illustration are shown being spherical, any or all of the balancing and valve chambers could have an alternative shape, such as an elliptical or oblong shape.

One or more flexible membrane or sheeting 190, 192 is located between pneumatic caps 262a, 264a and upper fluid balancing chamber 290a and the respective chambers of fluid pieces 280a. Membranes or sheeting 190, 192 may be made of polyvinyl chloride ("PVC"), polyethylene, kraton or polyolefin, for example, or of another medically safe flexible plastic or rubber. Membranes or sheeting 190, 192 may be flat and caused to stretch during actuation or be preformed or predomed to have a shape the same as or similar to pneumatic caps 262a, 264a and/or fluid valve chambers 282a, 284a, so that membranes or sheeting 190, 192 do not stretch and instead flap back and forth. Membranes or sheeting 190, 192 for balancing chambers 286a, 290a are in one embodiment flat.

Any one or more of (i) pressure checks, (ii) electrical contact sensors, (ii) capacitive or inductive sensors, or (iii) a memory storing a known pressure spike that occurs when a non-leaking membrane 190, 192 may again be used to prevent leaking fluid from entering pneumatic manifold 240a. Pneumatic operation of the valves operates the same as described in FIG. 3.

Fluid manifold 300a for balance chamber portion 86a, 86b of medical fluid management assembly 110a, 110b or 110c includes a fluid pathway plate 302a heat sealed, sonically sealed, or solvent bonded to a cover plate 320a. Plates 302a and 320a may each be made of a rigid, medically safe plastic, such as, polyethylene ("PE"), polypropylene ("PP"), polyvinyl chloride ("PVC"), polysulfone, polystyrene, polycarbonate ("PC"), acrylic, cyclo-olefin copolymers ("COCs"), acrylonitrile butadiene styrene ("ABS"), polyolefin and the like.

Fluid pathway plate 302a includes or defines a first fluid pathway 304a and a second fluid pathway 306a. Fluid pathway plate 302a further defines a first valve o-ring seat 308a for sealingly holding a first valve o-ring 144. Fluid pathway plate 302a further defines a second valve o-ring seat 310a for sealingly holding a second valve o-ring 144. Any fluid pathway discussed herein, such as fluid outlet pathway 306a, may be fitted with a one-way valve or check valve 212.

Cover plate 320a is permanently sealed to fluid pathway plate 302a in one embodiment, so that separate gasketing is not needed to seal first fluid pathway 304a or second fluid pathway 306a. Cover plate 320a may include a raised or buttressed section 322a to help hold and seal check valve 212 in place. In the illustrated embodiment, first fluid valve chamber 282a and second fluid valve chamber 284a each define a fluid port that fits sealingly within a respective o-ring 144 and abuts against a mating fluid pathway, e.g., first fluid pathway 304*a* and second fluid pathway 306*a*, to provide a fluid-tight connection between valve engine 260*a* and fluid manifold 300*a*.

Fluid, such as water, liquid concentrate, dialysis fluid or blood flows through balancing chambers 86*a*, 86*b* as follows. As discussed above, balancing chambers 286*a* and 290*a*, separated by membranes 190, 192, are associated with four valves, left and right valves visible in FIG. 6 and left and right valves behind the visible valves in FIG. 6. One of the left or right visible valves is an inlet valve to lower balancing chamber 286*a*, while the other of the left or right visible valves is an outlet valve to lower balancing chamber 286*a*. The same applies to the hidden valves, but for upper balancing chamber 290*a*. One of the left or right hidden valves is an inlet valve to upper balancing chamber 290*a*, while the other of the left or right hidden valves is an outlet valve to upper balancing chamber 290*a*. Depending upon how balancing chambers 86*a*, 86*b* are positioned relative to other components of medical fluid management assembly 110*a*, 110*b* or 110*c*, it may be more convenient to have (i) both left valves be inlet valves and both right valves be outlet valves, (ii) both left valves be outlet valves and both right valves be inlet valves, (iii) left visible valve be an inlet valve, right visible valve be an outlet valve, left hidden valve be an outlet valve and right hidden valve be an inlet valve, or (iv) left visible valve be an outlet valve, right visible valve be an inlet valve, left hidden valve be an inlet valve and right hidden valve be an outlet valve.

Figure 7:
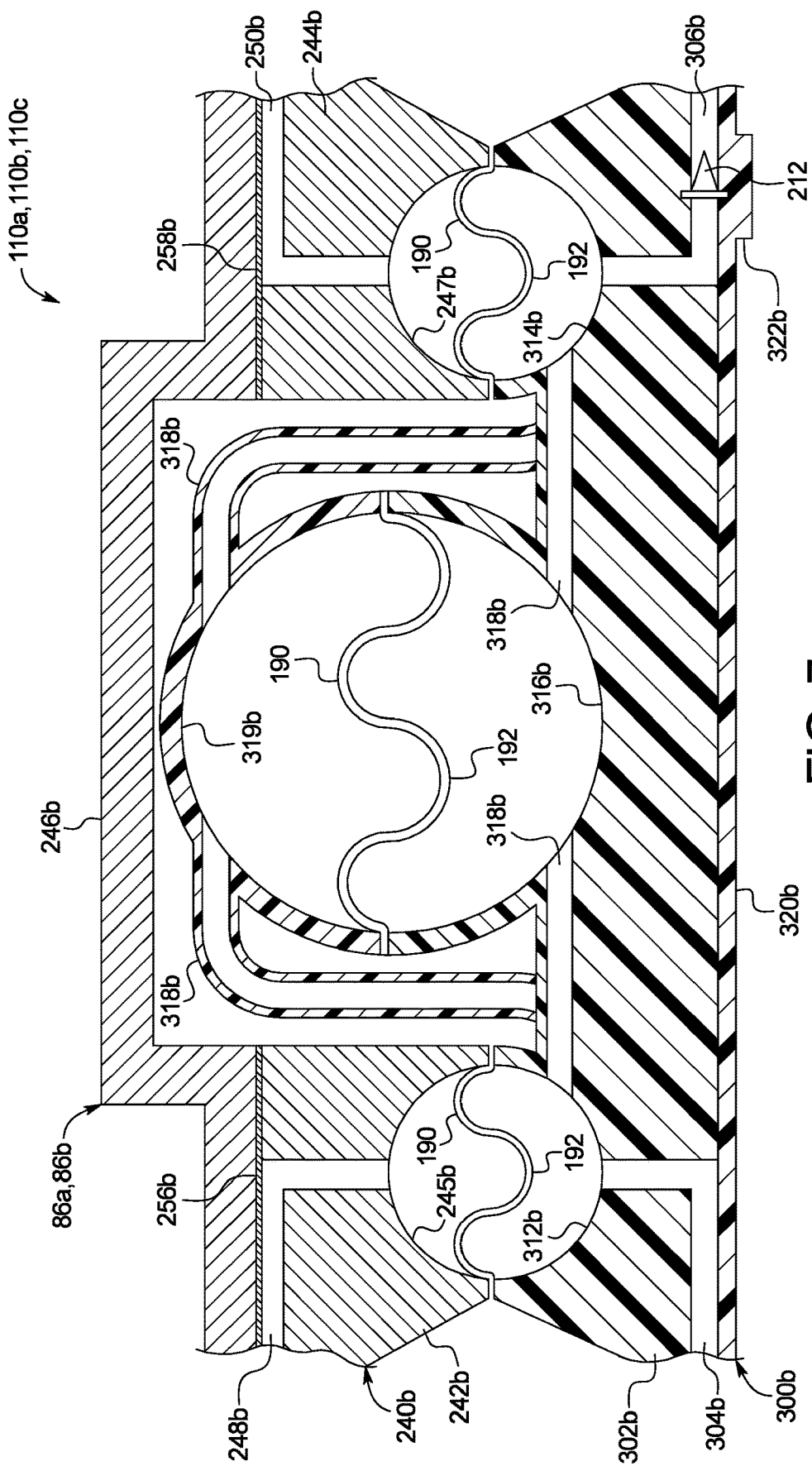
FIG. 7 is a side sectioned view of another embodiment for a balance chamber for any of the medical fluid management assemblies of the present disclosure.

Referring now to FIG. 7, a cross-sectional view of another embodiment of a balance chamber portion 86*a*, 86*b* for inclusion with any of fluid management assemblies 110*a* to 110*c* discussed above is illustrated. Balance chamber portion 86*a*, 86*b* of FIG. 7 in the illustrated embodiment includes two primary components, namely, a pneumatic manifold 240*b* and a fluid manifold 300*b*. Valve engine 260*a* of FIG. 6 has been eliminated.

Pneumatic manifold 240*b* in an embodiment includes metal plates or pieces 242*b*, 244*b* and 246*b*, which may be machined aluminum, steel, stainless steel and combinations thereof. Where abutted, plates or pieces 242*b*, 244*b* and 246*b* may be bolted removeably together using bolts and nuts and/or female mating threads.

Plate 242*b* defines a pneumatic valve groove 248*b* for carrying positive and negative pressure (or vent to atmosphere) selectively to a first pneumatic valve chamber 245*b* also defined by plate 242*b*. Plate 244*b* defines a pneumatic valve groove 250*b* for carrying positive and negative pressure (or vent to atmosphere) selectively to a second pneumatic valve chamber 247*b* also defined by plate 244*b*. There is again no pneumatic connection to the upper balancing chamber 290*b* of balance chamber 86*a*, 86*b* because upper chamber 290*b* carries liquid.

All pneumatic o-ring seats and associated o-rings 144 of FIG. 6 are eliminated.

A gasket 256*b* is compressed between plate 242*b* and plate 246*b* to seal pneumatic grooves or passageways formed in plate 242*b* and/or plate 246*b*, e.g., groove or passageway 248*b*. A gasket 258*b* is compressed between plate 244*b* and plate 246*b* to seal pneumatic grooves or passageways formed in plate 244*b* and/or plate 246*b*, e.g., groove or passageway 250*b*. Gaskets 256*b* and 258*b* may be compressible silicone for example. The pneumatic grooves or passageways lead to electrically actuated pneumatic solenoid valves (not illustrated) as discussed above, which may be spring closed when non-energized and opened when energized. The electrically actuated pneumatic solenoid valves may be mounted to pneumatic manifold 240*b*.

Fluid manifold 300*b* for balance chamber portion 86*a*, 86*b* of medical fluid management assembly 110*a*, 110*b* or 110*c* includes a fluid pathway plate 302*b* heat sealed, sonically sealed, or solvent bonded to a cover plate 320*b*. Plates 302*b* and 320*b* may each be made of a rigid, medically safe plastic, such as, polyethylene ("PE"), polypropylene ("PP"), polyvinyl chloride ("PVC"), polysulfone, polystyrene, polycarbonate ("PC"), acrylic, cyclo-olefin copolymers ("COCs"), acrylonitrile butadiene styrene ("ABS"), polyolefin and the like.

Fluid pathway plate 302*b* includes or defines a first fluid pathway 304*b* and a second fluid pathway 306*b*. Fluid valve o-ring seats and associated o-rings 144 of FIG. 6 have been eliminated. Any fluid pathway discussed herein, such as fluid outlet pathway 306*a*, may be fitted with a one-way valve or check valve 212. Cover plate 320*b* is permanently sealed to fluid pathway plate 302*b* in one embodiment, so that separate gasketing is not needed to seal first fluid pathway 304*b* or second fluid pathway 306*b*. Cover plate 320*b* may include a raised or buttressed section 322*b* to help hold and seal check valve 212 in place.

In the illustrated embodiment, fluid pathway plate 302*b* defines a first fluid valve chamber 312*b* and a second fluid valve chamber 314*b*. First fluid valve chamber 312*b* mates with first pneumatic valve chamber 245*b*. Second fluid valve chamber 314*b* mates with second pneumatic valve chamber 247*b*. First fluid valve chamber 312*b* communicates fluidly with a lower balancing chamber 316*b* via a first fluid tube section 318*b*, while second fluid valve chamber 314*b* communicates fluidly with lower balancing chamber 316*b* via a second fluid tube section 318*b*. Lower balancing chamber 316*b*, first and second fluid tube sections 318*b* are each formed by or in fluid pathway plate 302*b* in the illustrated embodiment.

First and second hidden fluid valve chambers are located behind first and second visible chambers 312*b* and 314*b*. First hidden fluid valve chamber communicates fluidly with an upper balancing chamber 319*b* via a third fluid tube section 318*b*, while second hidden fluid valve chamber communicates fluidly with upper balancing chamber 319*b* via a fourth fluid tube section 318*b*. Third and fourth fluid tube sections 318*b* are in one embodiment each heat sealed, sonically welded, or solvent bonded to fluid pathway plate 302*b* and upper balancing chamber 319*b*, which is in turn heat sealed, sonically welded, or solvent bonded to lower balancing chamber 316*b*. Third and fourth fluid tube sections 318*b* are in an alternative embodiment pressed sealingly into o-rings 144 (not illustrated) fitted to fluid pathway plate 302*b*, such that upper balancing chamber 319*b* (permanently welded, heat sealed or adhered to third and fourth fluid tube sections 318*b*) is in turn pressed sealingly onto lower balancing chamber 316*b* and held in place via plate 246*b*.

It should again be appreciated that while the balancing and valve chambers for ease of illustration are shown being spherical, any or all of the balancing and valve chambers could have an alternative shape, such as an elliptical or oblong shape.

One or more flexible membrane or sheeting 190, 192 is located between pneumatic valve chambers 245*b*, 247*b* and upper fluid balancing chamber 319*b* and the respective chambers 312*b*, 314*b* and 316*b* of fluid pathway plate 302*b*. Membranes or sheeting 190, 192 may be made of polyvinyl chloride ("PVC"), polyethylene, kraton or polyolefin, for example, or of another medically safe flexible plastic or rubber. Membranes or sheeting 190, 192 may be flat and caused to stretch during actuation or be preformed or predomed to have a shape the same as or similar to pneumatic valve chambers 245b, 247b and/or fluid valve chambers 312b, 314b, so that membranes or sheeting 190, 192 do not stretch and instead flap back and forth. Membranes or sheeting 190, 192 for balancing chambers 316b, 319b are in one embodiment flat but may alternatively be pre-domed or preshaped.

Any one or more of (i) pressure checks, (ii) electrical contact sensors, (ii) capacitive or inductive sensors, or (iii) a memory storing a known pressure spike that occurs when a non-leaking membrane 190, 192 may again be used to prevent leaking fluid from entering pneumatic manifold 240b. Pneumatic operation of the valves operates the same as described in FIG. 3.

Fluid, such as water, liquid concentrate, dialysis fluid or blood flows through balancing chambers 86a, 86b as described above for FIG. 6, where balancing chambers 316b and 319b in FIG. 7 replace balancing chambers 286a and 290a, respectively, in FIG. 6.

Figure 8:
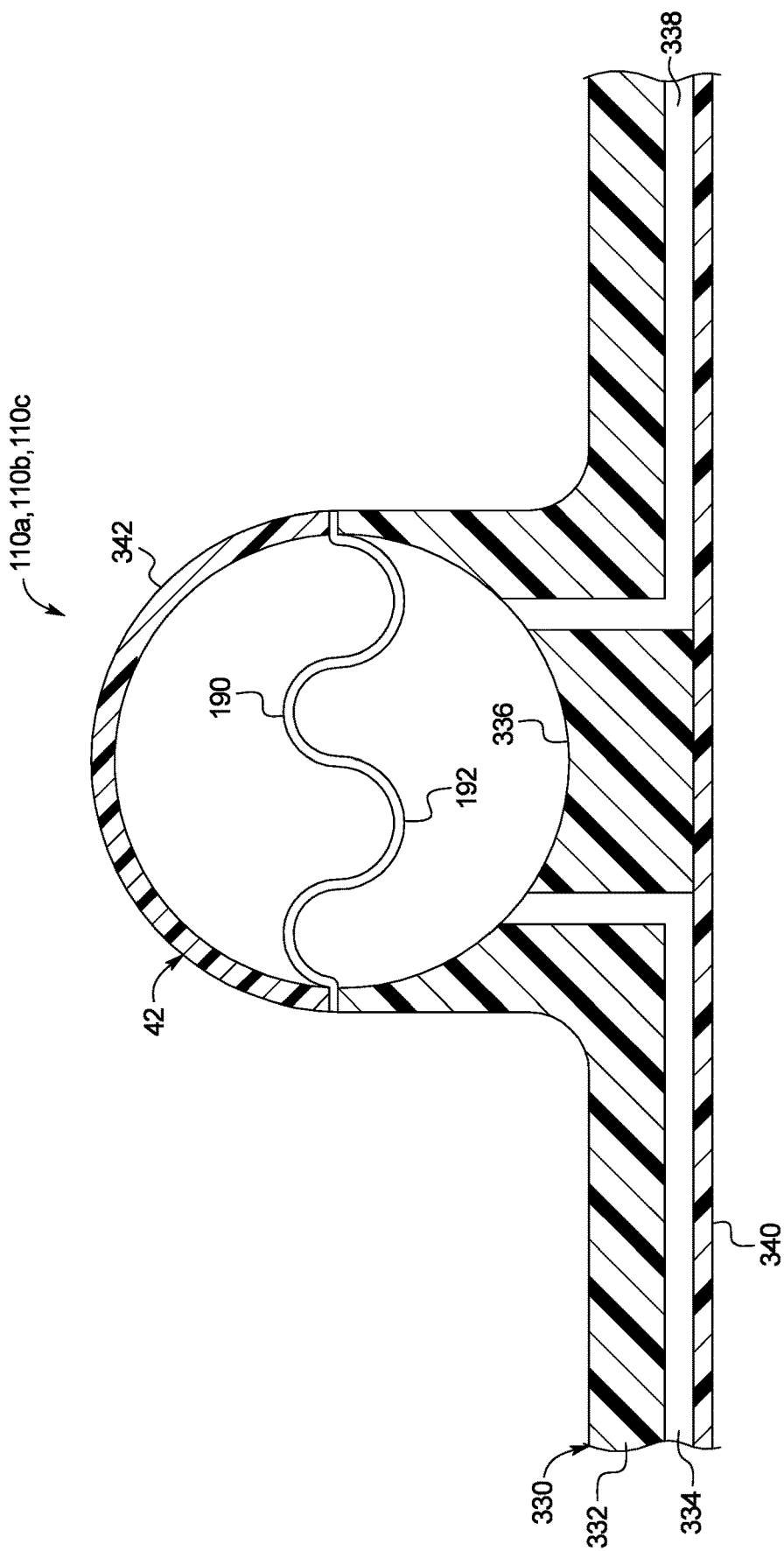
FIG. 8 is a side sectioned view of one embodiment for a water accumulator for any of the medical fluid management assemblies of the present disclosure.

Referring now to FIG. 8, a cross-sectional view of an embodiment of a water accumulator portion 42 for inclusion with any of fluid management assemblies 110a to 110c discussed above is illustrated. Water accumulator portion 42 of FIG. 8 in the illustrated embodiment includes only a fluid manifold 330. Fluid manifold 330 includes a fluid pathway plate 332 sealed to a cover plate 340. Fluid pathway plate 332 defines water inlet pathway 334 leading to a water chamber 336 and water outlet pathway 338 leading from water chamber 336. Water chamber 336 is permanently sealed or in sealed compression with an air chamber plate 342.

Fluid pathway plate 332, cover plate 340 and air chamber plate 342 may each be made of a rigid, medically safe plastic, such as, polyethylene ("PE"), polypropylene ("PP"), polyvinyl chloride ("PVC"), polysulfone, polystyrene, polycarbonate ("PC"), acrylic, cyclo-olefin copolymers ("COCs"), acrylonitrile butadiene styrene ("ABS"), polyolefin and the like. Fluid pathway plate 332 may be heat sealed, sonically sealed, or solvent bonded to both cover plate 340 and air chamber plate 342. Air chamber plate 342 may alternatively be held in compression onto water chamber 336. In either case, one or more flexible membrane 190, 192 is compressed between water chamber 336 air chamber plate 342.

Flexible membrane 190, 192 may be made of any of the materials discussed above and stretches to allow more or less water into water chamber 336. Flexible membrane 190, 192 also tends to dampen pulsatility in the flow of water to the mixing portion of machine 90.

Figure 9:
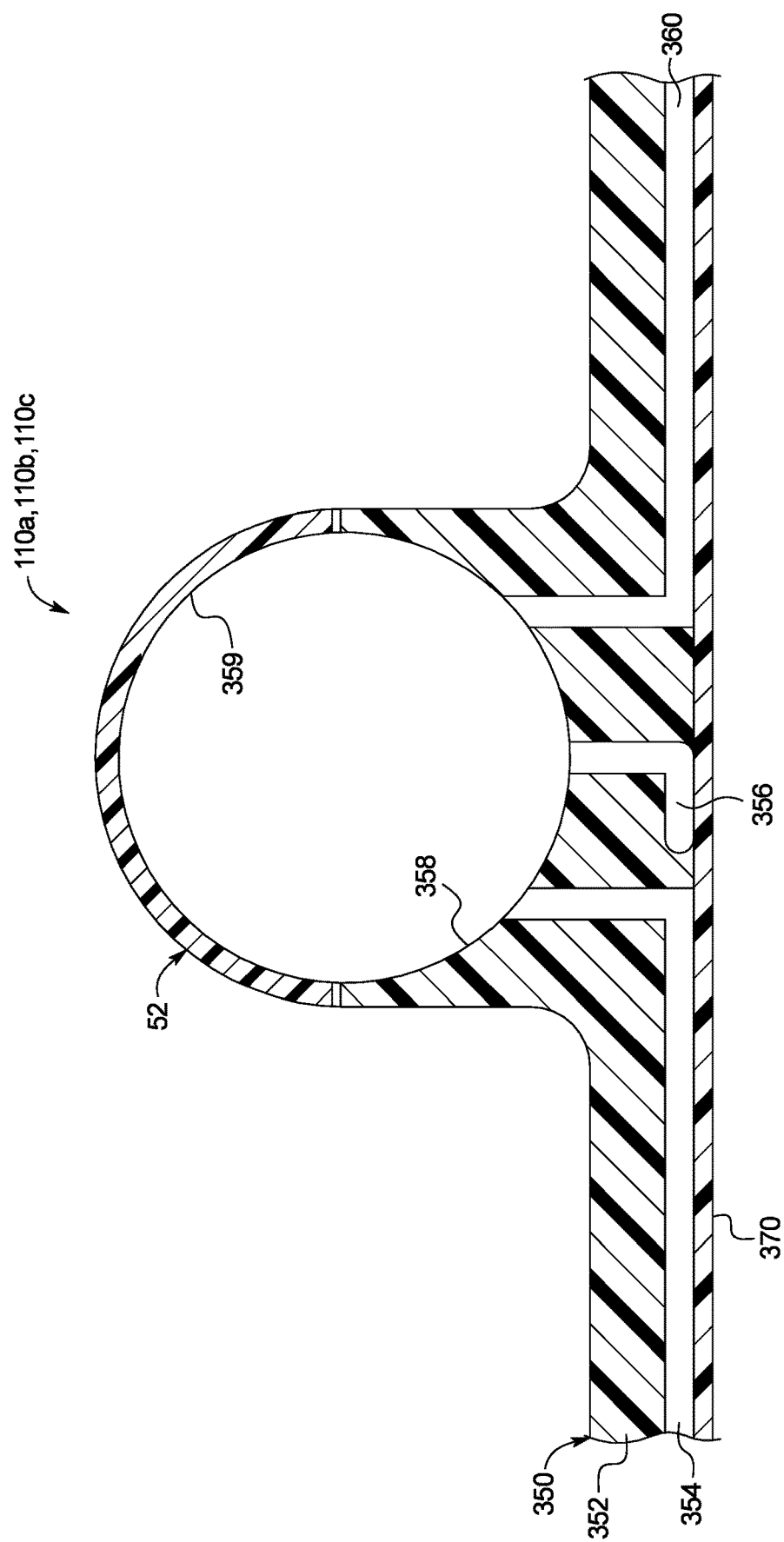
FIG. 9 is a side sectioned view of one embodiment for a mixing chamber for any of the medical fluid management assemblies of the present disclosure.

Referring now to FIG. 9, a cross-sectional view of an embodiment of a mixing chamber 52 for inclusion with any of fluid management assemblies 110a to 110c discussed above is illustrated. Mixing chamber portion 52 of FIG. 9 in the illustrated embodiment includes only a fluid manifold 350. Fluid manifold 350 includes a fluid pathway plate 352 sealed in any manner discussed above to a cover plate 370. Fluid pathway plate 352 defines water/bicarbonate mixture inlet pathway 354 and a liquid acid inlet pathway 356 leading to a mixing chamber housing 358, and a mixed dialysis fluid outlet pathway 360 leading from mixing chamber housing 358 to a desired destination.

Fluid pathway plate 352, cover plate 360 may each be made of a rigid, medically safe plastic, such as, polyethylene ("PE"), polypropylene ("PP"), polyvinyl chloride ("PVC"), polysulfone, polystyrene, polycarbonate ("PC"), acrylic, cyclo-olefin copolymers ("COCs"), acrylonitrile butadiene styrene ("ABS"), polyolefin and the like. Fluid pathway plate 352 may be heat sealed, sonically sealed, or solvent bonded to both cover plate 360. Here, no flexible membrane 190, 192 is used.

Mixing chamber allows water that has been pre-mixed with bicarbonate, e.g., dry bicarbonate powder to mix with a metered amount of liquid acid to produce fresh dialysis fluid for use within machine 90.

Figure 10:
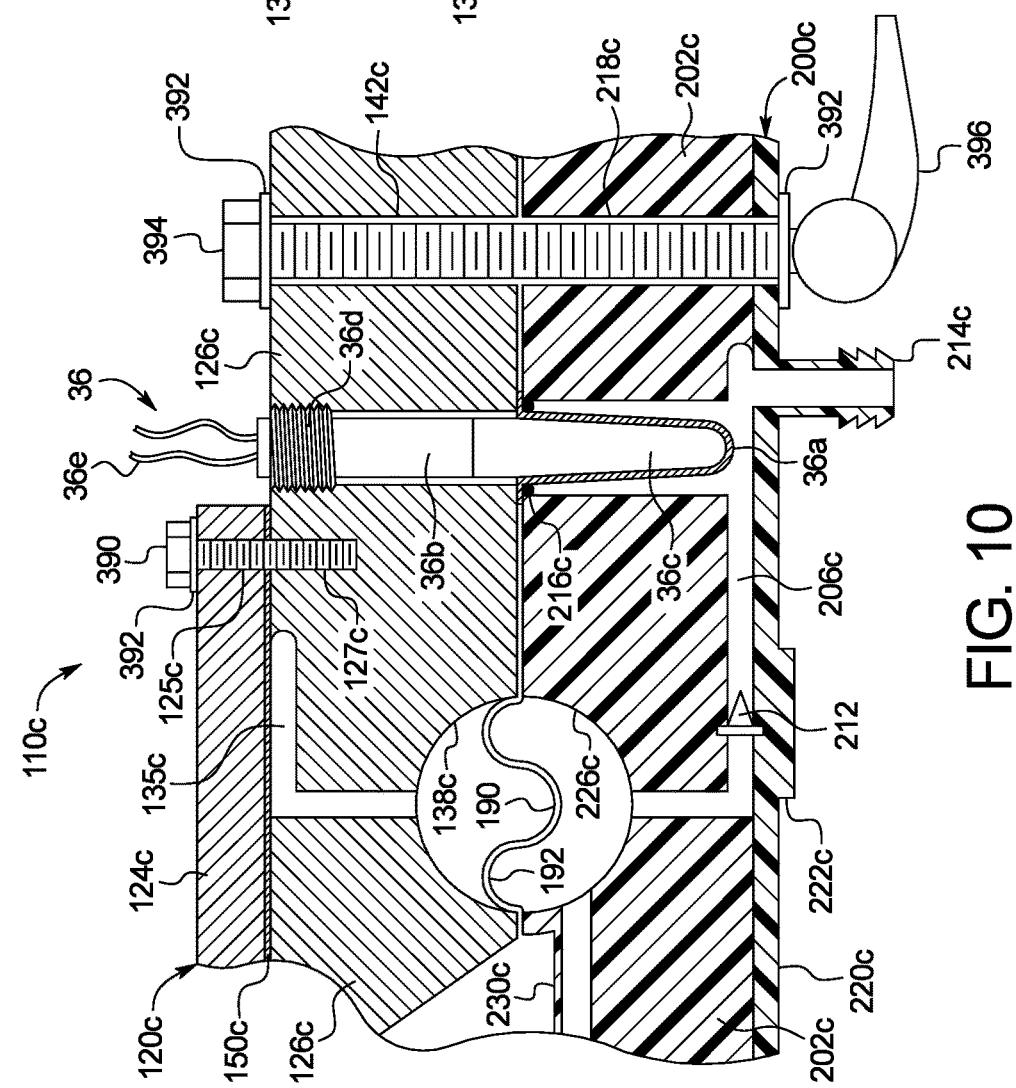
FIG. 10 is a side sectioned view of one embodiment for a conductivity probe integrated with an example medical fluid management assembly of the present disclosure, and of one embodiment for holding together the various components fluid management assemblies.

Referring now to FIG. 10, one embodiment for integrating a conductivity sensor 36 into the medical fluid management assemblies of the present disclosure is illustrated. Conductivity sensors 36 are illustrated additionally in connection with FIG. 12 below. Conductivity sensors 36 are illustrated as being integrated into fluid management assembly 110c of FIG. 5. Each of the element numbers illustrated in FIG. 10 that is also illustrated in FIG. 5 includes all of the structure, functionality and alternatives discussed above for, or incorporated by reference into the discussion of, FIG. 5. It should also be appreciated that conductivity sensors 36 may likewise be integrated in the manner discussed in connection with FIG. 10 into fluid management assemblies 110a and 110b of FIGS. 3 and 4, respectively.

FIG. 10 illustrates that fluid pathway 206c leads to an inlet or outlet port 214c, which connects sealingly to a tube via a hose barb connection in the illustrated embodiment. Viewing FIG. 12 and the example placement of conductivity sensors 36, the tube may for example be purified water line 62, the tube from acid pump 74 or the tube leading to or from water pump 52. Conductivity sensor 36 in the illustrated embodiment is placed in fluid outlet pathway 206c between pneumatic outlet valve chamber 138c/fluid outlet valve chamber 226c and inlet or outlet port 214c. In an alternative embodiment, conductivity sensor 36 is located upstream of inlet port 214c or downstream of outlet port 214c.

Conductivity sensor 36 in the illustrated embodiment includes an insert 36a, e.g., a somewhat cone or conical-shaped insert, which is placed in sealed engagement with fluid pathway plate 202c via a compressed o-ring 216c. Alternatively, insert 36a may be molded into plate 202c. In an embodiment, insert 36a is discarded when fluid manifold 200c is discarded, which may be after a single use or multiple uses, e.g., a month's worth of uses. Insert 36a is made of a conductive, medically safe material, such as stainless steel or titanium.

Conductivity probe 36b is carried instead by metal plate or piece 126c of pneumatic manifold 120c. Probe 36b is likewise made of a conductive material, such as copper, steel, aluminum or stainless steel. Probe 36b is not intended to come into contact with medical fluid or any of the fluids discussed herein. Probe 36b includes an insert end 36c, which is cone or conical-shaped to contact and match that of insert 36a. Conductivity probe 36b includes a threaded end 36d, which threads into place with mating threads formed in a bore in metal plate or piece 126c of pneumatic manifold 120c. Sensing leads 36e lead from threaded end 36d to control unit 50 (FIG. 1). Probe 36b may be reused for as long as it operates properly. Thus only the small, thin conductive probe 36a need be discarded, which again may result after multiple uses. Conductivity sensors 36 of the present disclosure therefore do not add significant disposal cost.

Figure 12:
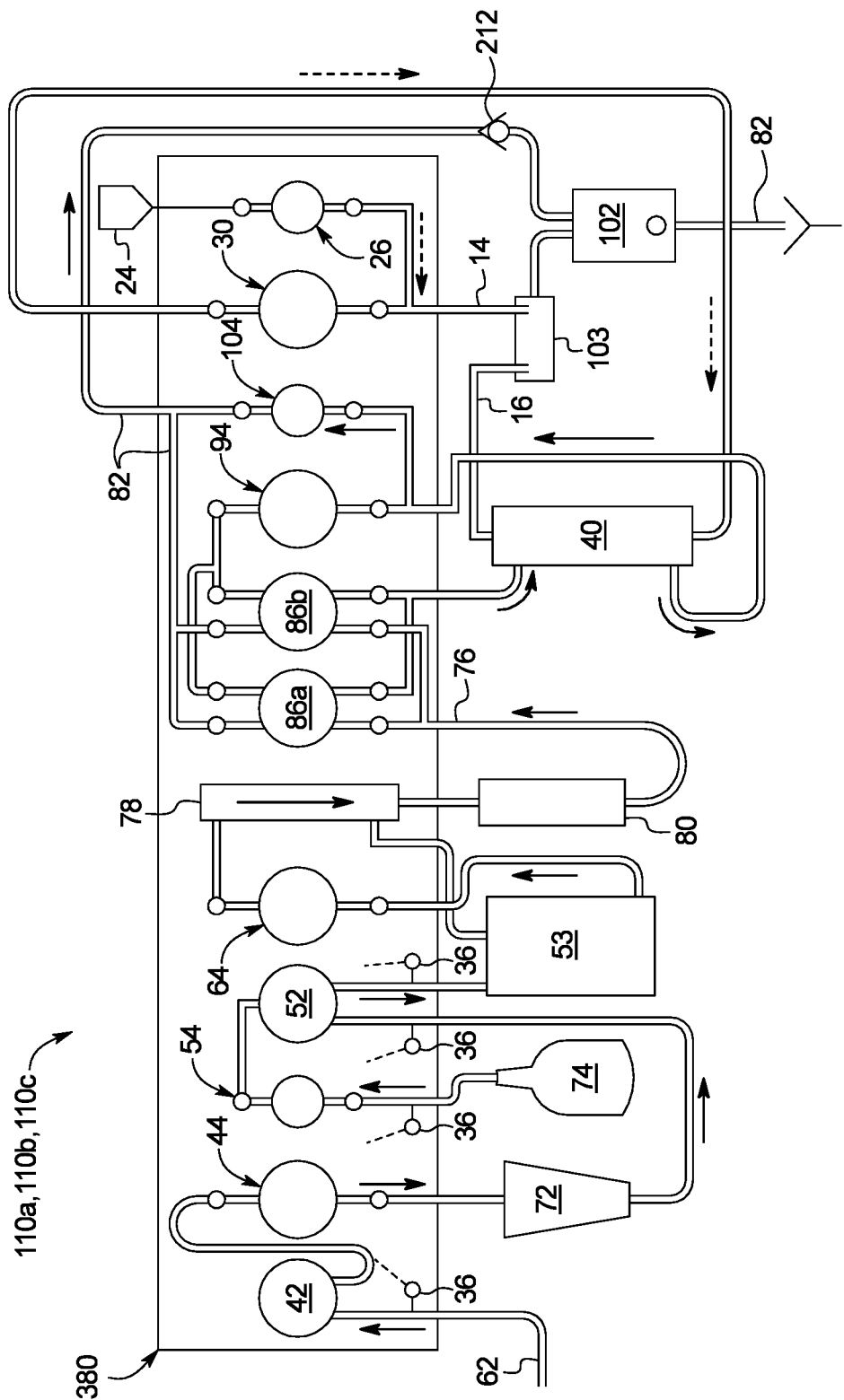
FIG. 12 is a schematic view of one embodiment for assimilating the structures of FIGS. 3 to 11 to form any of the medical fluid management assemblies of the present disclosure.

The conductivity of the fluid traveling through fluid pathway 206c is detectable via insert 36a contacting conductive probe rod 36b, having conductive leads extending to control unit 50. In an embodiment, each conductivity sensor 36 illustrated in FIG. 12 is actually a pair of sensors, e.g., two of the sensors 36 illustrated in FIG. 10. One sensor of the pair further includes thermistor or thermocouple wires compressed between mating conductive insert 36a and conductive probe 36b for sensing the fluid temperature at the point where the conductivity reading is taken. In this manner, control unit 50 may input the relevant fluid temperature to provide a temperature compensated conductivity reading.

FIG. 10 also illustrates embodiments for securing pneumatic manifold 120c and fluid manifold 200c together, so as to compress gaskets 146c, 148c, 150c, and flexible membranes 190 and 192 to provide an airtight and fluid-tight fluid management assembly 110c. The embodiments discussed in connection with FIG. 10 also compress gaskets 144 illustrated in FIGS. 3 and 4 to provide airtight and fluid-tight fluid management assemblies 110a and 110b.

In the illustrated embodiment, the different plates or pieces of pneumatic manifold 120c are metal and may thus be threaded. FIG. 10 shows that metal plate or piece 124c defines a through-bore that allows threads of a bolt or fastener 390 to pass through metal plate or piece 124c to reach mating female threads of a threaded bore 127c formed in plate 126c. Bolt or fastener 390 may be fastened with one or both flat and lock washers 392. Multiple bolts or fasteners 390 are provided as needed to compress gaskets 146c, 148c, 150c, thereby sealing pneumatic passageways, such as passageway 135c illustrated in FIG. 10. Bolts or fasteners 390 only need to be removed from pneumatic manifold 120c if it needs maintenance, e.g., upon a fluid leak into pneumatic passageways, such as passageway 135c. Pneumatic manifolds 120a and 120b of FIGS. 3 and 4 respectively may be held together in the same manner using bolts or fasteners 390.

Fluid manifolds 200a, 200b and 200c of FIGS. 3, 4, 5 and 10, respectively, and are each held together via heat seal, sonic seal, or solvent bonding in various embodiments. The sealing together of (i) the pump and valve engine 160a, and the pump and valve engine 160a to pneumatic manifold 120a and fluid manifold 200a in FIG. 3, (ii) the pump and valve engine 160b, and the pump and valve engine 160b to fluid manifold 200b in FIG. 4, and (iii) pneumatic manifold 120c and fluid manifold 200c in FIGS. 5 and 10 is performed using longer bolts or fasteners 394 illustrated in FIG. 10. Again, FIG. 10 illustrates situation (iii) pneumatic manifold 120c sealing to fluid manifold 200c.

In FIG. 10, plate 126c of pneumatic manifold 120c defines a bore or aperture 142c, while fluid pathway plate 202c of fluid manifold 200c defines a mating bore or aperture 218c. Mating bores or apertures 142c and 218c accept bolt or fastener 394. A quick disconnect 396 (e.g., a bicycle style quick clamp) is provided on the outside of fluid manifold 200c, so that a user may quickly release quick disconnect 396 and pull fluid manifold 200c from pneumatic manifold 120c, which is bolted or otherwise connected to machine 90 in one embodiment. Multiple fasteners 394 (including one or both of flat and lock washers 392) are coupled via quick disconnects 396 to enable the user to quickly undue disconnects 396 and swap out fluid manifold 200c when needed. In an embodiment, flexible membranes 190 and 192 are provided with fluid manifold 200c so that new membranes are provided with a new manifold 200c. With fluid management assemblies 110a and 110b, the pump and valve engines and the fluid manifolds would be swapped out upon releasing quick disconnects 396.

It should be appreciated that other types of quick disconnects may be used. Further alternatively, quick disconnects may be replaced by nuts or locknuts, wherein the user uses a tool to remove the nuts to swap out the appropriate pump and valve engines and/or fluid manifolds.

Figure 11:
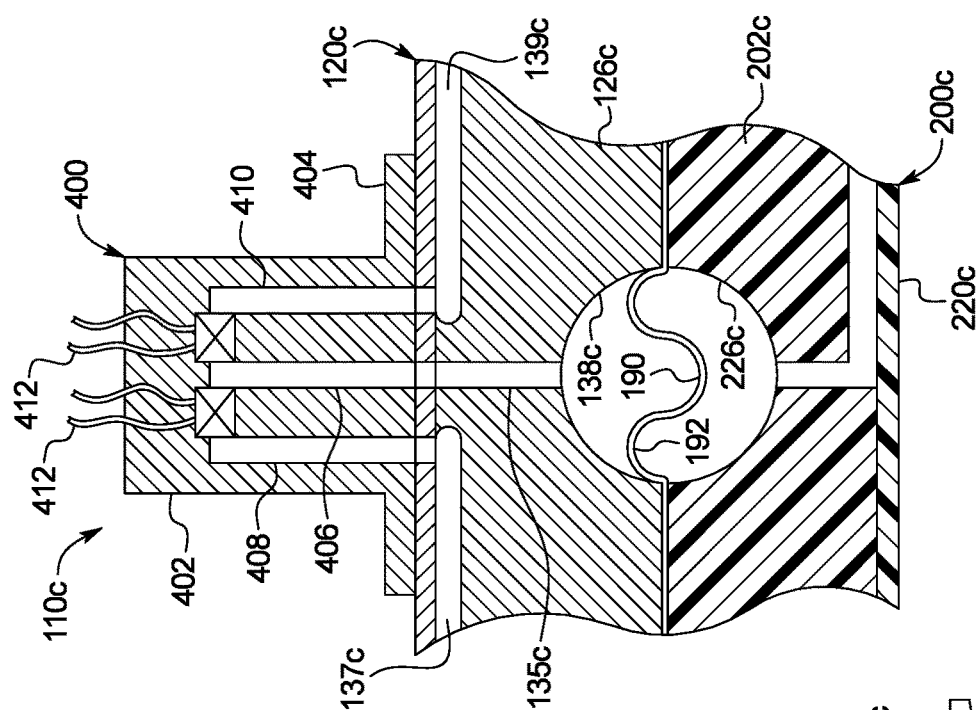
FIG. 11 is a side sectioned view of one embodiment for integrating an electrically actuated pneumatic valve with an example medical fluid management assembly of the present disclosure.

Referring now to FIG. 11, one embodiment for integrating an electrically actuated pneumatic valve 400 into the medical fluid management assemblies of the present disclosure is illustrated. Electrically actuated pneumatic valves 400 are illustrated as being integrated into fluid management assembly 110c of FIG. 5. Each of the element numbers illustrated in FIG. 11 that is also illustrated in FIG. 5 includes all of the structure, functionality and alternatives discussed above for, or incorporated by reference into the discussion of, FIG. 5. It should also be appreciated that electrically actuated pneumatic valve 400 may likewise be integrated in the manner discussed in connection with FIG. 11 into fluid management assemblies 110a and 110b of FIGS. 3 and 4, respectively.

Pneumatic passageway 135c is provided again to deliver positive or negative pneumatic pressure to pneumatic valve chamber 138c (inlet tor outlet) of plate 126c. In FIG. 11, positive groove or passageway 137c and negative groove or passageway 139c are added so that valve 400 may supply either positive or negative pneumatic pressure to pneumatic passageway 135c and pneumatic valve chamber 138c. It should be appreciated that negative groove or passageway 139c may alternatively be a passageway to atmosphere. That is, instead of using negative pressure to open flexible membranes 190 and 192, membranes after being closed via positive pressure may instead be vented to atmosphere, allowing positive fluid pressure on the other side of the membranes open the valve. If, however, groove or passageway 139c is to be used for negative pressure, then the passageway is connected pneumatically to a source of negative pressure, such as a negative pressure reservoir or a negative pressure manifold. Likewise, positive groove or passageway 137c is connected pneumatically to a source of positive pressure, such as a positive pressure reservoir or a positive pressure manifold.

Electrically actuated pneumatic valve 400 may be of different forms. For pneumatic valves chambers, such as pneumatic valve chamber 138c, pneumatic valve 400 may be an on/off type valve using electrically actuated solenoids 412 that either open or close pneumatic passageway 135c and pneumatic valve chamber 138c to positive pressure or negative pressure (or vent). In an embodiment, electrically actuated solenoids 412 are normally closed and require electrical energy to open valve chamber 138c to positive or negative pressure. In this manner, no actuation occurs upon power loss. As discussed above, flexible membranes 190 and 192 may be preshaped or predomed, and may be positioned so that membranes 190 and 192 are closed against fluid valve chamber 226c upon power loss.

For pneumatic pump chambers, such as pneumatic pump chamber 140c of FIG. 5, pneumatic valve 400 may be a variable orifice valve, which is commanded by control unit 50 (FIG. 1) to allow a varying amount of positive or negative pneumatic pressure to pneumatic pump chamber 140c. Regardless of which type of valve 400 is used, positive pressure in FIG. 11 is supplied through positive groove or passageway 137c, through positive valve inlet 408 and valve outlet 406, to pneumatic passageway 135c and pneumatic valve chamber 138c. Likewise, regardless of which type of valve 400 is used, negative pressure in FIG. 11 is supplied through negative groove or passageway 139c, through negative valve inlet passageway 410 and valve outlet passageway 406, to pneumatic passageway 135c and pneumatic valve chamber 138c.

FIG. 11 illustrates that pneumatic valves 400 may be mounted sealingly and directly to the fluid management assemblies of the present disclosure, such as fluid management assembly 110c of FIGS. 5 and 11. As illustrated, this configuration allows pneumatic passageways (e.g., passageway 135c) between valves 400 and their respective pneumatic chambers (e.g., chamber 138c) to be as short as possible. Positive passageway 137c and negative passageway 139c may be manifold lines supplying many valves. In this way, pneumatic routing for the fluid management assemblies of the present disclosure may be minimized.

Referring now to FIG. 12, an overall view of one embodiment for fluid management assembly 110a (using pumps according to FIG. 3), 110b (using pumps according to FIG. 4) or 110c (using pumps according to FIG. 5), any of which employs balance chambers according to FIG. 6 or 7, a water accumulator according to FIG. 8 and a mixing chamber according to FIG. 9 is illustrated. Fluid management assembly 110a to 110c includes an overall fluid manifold 380, which may be considered to be a combination or amalgamation of fluid manifolds 200a/200b/200c, 300a/300b, 330 and 350 discussed above along with the definition of other fluid pathways discussed below.

Fresh water is introduced via purified water line 62 into overall fluid manifold 380 at water accumulator 42 provided according to FIG. 9 in one embodiment. Purified water is pump via water pump 44, provided according to any of FIGS. 3 to 5, into a bicarbonate cartridge 72, which is located separate from fluid manifold 380, within machine 90. At the same time, a liquid acid pump 54, provided according to any of FIGS. 3 to 5, pumps liquid acid concentrate from a container 74, which is located separate from fluid manifold 380, within machine 90.

FIG. 12 illustrates that fluid manifold 380 provides space for conductivity sensors 36 to measure the conductivity of fluids at pertinent locations, such as in water line 62, downstream of bicarbonate cartridge 72, in the liquid acid line, and downstream from mixing chamber 52 where the conductivity of the resulting fresh dialysis fluid should reside within a set range. Conductivity sensors 36 show dashed lines indicating that they communicate information with control unit 50 (FIG. 1). Control unit 50 evaluates the signals form conductivity probes to evaluate whether and ensure that dialysis fluid is mixed properly.

Fresh dialysis fluid is pumped to a dialysis fluid holding tank 53, which is located separate from fluid manifold 380, within machine 90. Fresh dialysis fluid pump 64, provided according to any of FIGS. 3 to 5, pumps fresh dialysis fluid from holding tank 53, through ultrafilter 78, which is mounted to fluid manifold 380 and placed in fluid-tight communication with fluid located in fluid manifold 380. Ultrafilter 78 as illustrated outputs further purified dialysis fluid to heater 80 and rejects a portion of dialysis fluid back to dialysis fluid holding tank 53. Heater 80 is located separate from fluid manifold 380, within machine 90.

Fresh, heated dialysis fluid is pumped via fresh dialysis fluid pump 64 to balance chambers 86a and 86b. Balance chambers 86a and 86b may be provided according to any of FIG. 6 or 7. Used dialysis fluid is pumped from dialyzer 40 via used dialysis fluid pump 94 to balance chambers 86a and 86b. Dialyzer 40 is located separate from fluid manifold 380, within machine 90. Used dialysis fluid pump 94 is provided according to any of FIGS. 3 to 5. Used dialysis fluid entering balance chambers 86a and 86b causes a like volume of fresh dialysis fluid to be delivered to dialyzer 40. Fresh dialysis fluid entering balance chambers 86a and 86b causes a like volume of used dialysis fluid to be delivered to drain via drain line 82.

UF pump 104, provided according to any of FIGS. 3 to 5, meters a precise and prescribed amount of used dialysis fluid as UF into drain line 82. Drain line 82 runs to a drain cassette 102 and then from drain cassette to house drain. Drain cassette 82 also connects fluidly with a blood tubing connector 103. Blood tubing connector 103, which may be provided on the front of machine 90 for easy user access, accepts arterial line 14 and venous line 16 when they are not connected to a patient 12 (FIG. 1), so that the dialysis fluid and blood circuits can be connected together for disinfection and priming. Because the disinfection and priming fluids have touched blood lines 14 and 16 that have carried the patient's blood, and because such fluids can reach drain cassette 102, drain cassette is provided separately from fluid manifold 380, so that if machine 90 is used for a different patient, only the small drain cassette 102 has to be replaced, manifold 380 can remain. To this end, a check valve 212 is placed in drain line 82 upstream of drain cassette so that fluid is prevented from backflowing from drain cassette into fluid manifold 380. As illustrated above, other check valves 212 may be integrated into overall fluid manifold 380.

FIG. 12 also illustrates that fluid management assembly 110a to 110c may also include blood pump 30 and heparin pump 26, which each may be provided according to any of FIGS. 3 to 5. Blood pump 30 pulls blood from arterial line 14 when connected to patient 12 and pushes the blood according to the arrow (dashed for blood, solid for dialysis fluid) through dialyzer 40 and venous line 16 when connected to patient 12. Heparin is pumped via heparin pump from vial 24 into arterial line 14 in one embodiment, according to the arrow (dash-dot for heparin).

FIG. 12 accordingly illustrates that most all fluid touching components of machine 90 may be placed on a single fluid manifold 380. It is envisioned that the only components described in FIG. 12 that reside outside the front of machine 10 are dialyzer 40, heparin vial 24, arterial line 14, venous line 16 and blood tubing connector 103, providing the machine with a sleek, simplified look. Water line 62 and drain line 82 may extend out the back of machine 90. In an alternative embodiment, blood pump 30 may also be viewed from the front of machine 90. It is contemplated that heparin vial 24 be replaced with a new vial each treatment, while blood set 100 is disinfected, reused and replaced approximately once every month. The remaining components of fluid manifold 380 may be replaced approximately every few, e.g., six, months.

Viewing FIG. 12 in light of FIGS. 3 to 9, it should be appreciated that the water pump 44, acid pump 54, fresh dialysis fluid pump 64, balance chambers 86a, 86b, used dialysis fluid pump 94, UF pump 104, blood pump 30 and heparin pump 26 have pneumatic components corresponding to the fluidic components of fluid manifold 380. Water accumulator 42, mixing chamber 52 and ultrafilter 78 do not have corresponding pneumatic components. It is therefore contemplated in one embodiment to provide water accumulator 42, mixing chamber 52 and ultrafilter 78 in a fluid management assembly different than assembly 110a to 110c of FIG. 12, so that pneumatic efficiently run only to fluid management assemblies needing pneumatic actuation. In alternative embodiment, different fluid management assemblies are separated according to use, e.g., water and mixing, versus dialysis fluid pumping, versus blood pumping. Further alternatively or additionally, different fluid management assemblies are separated according to whether they contain disposable versus reusable parts.

The twelve fluid components of fluid manifold 380 in FIG. 12 are laid out linearly, i.e., in a 12×1 array. In alternative embodiments, the twelve fluid components of fluid manifold 380 in FIG. 12 are still provided together but are laid out instead in a 6×2 array (split after ultrafilter 78), or in a 4×3 array (split after mixing chamber 52 and balance chambers 86a, 86b).

In still a further alternative embodiment, the twelve fluid components of fluid manifold 380 in FIG. 12 are split physically from each other, e.g., according to function, so that the separate manifolds and corresponding fluid management assemblies may be placed at desired locations within machine 90. For example, a first water and mixing fluid management assembly including water accumulator 42, water pump 44, acid pump 54 and mixing chamber 52 may be provided in a first location within machine 90, e.g., near bicarbonate cartridge 72 and acid container 74. A second dialysis fluid management assembly including fresh dialysis fluid pump 64, ultrafilter 78, balance chambers 86a, 86b, used dialysis fluid pump 94, and UF pump 104 may be provided in a second location within machine 90, e.g., near dialysis fluid holding tank 53. A third blood fluid management assembly including blood pump 30, heparin pump 26 and heparin vial 24 may be provided in a third location within machine 90, e.g., near dialyzer 40 and/or blood tubing connector 103.

Figure 13:
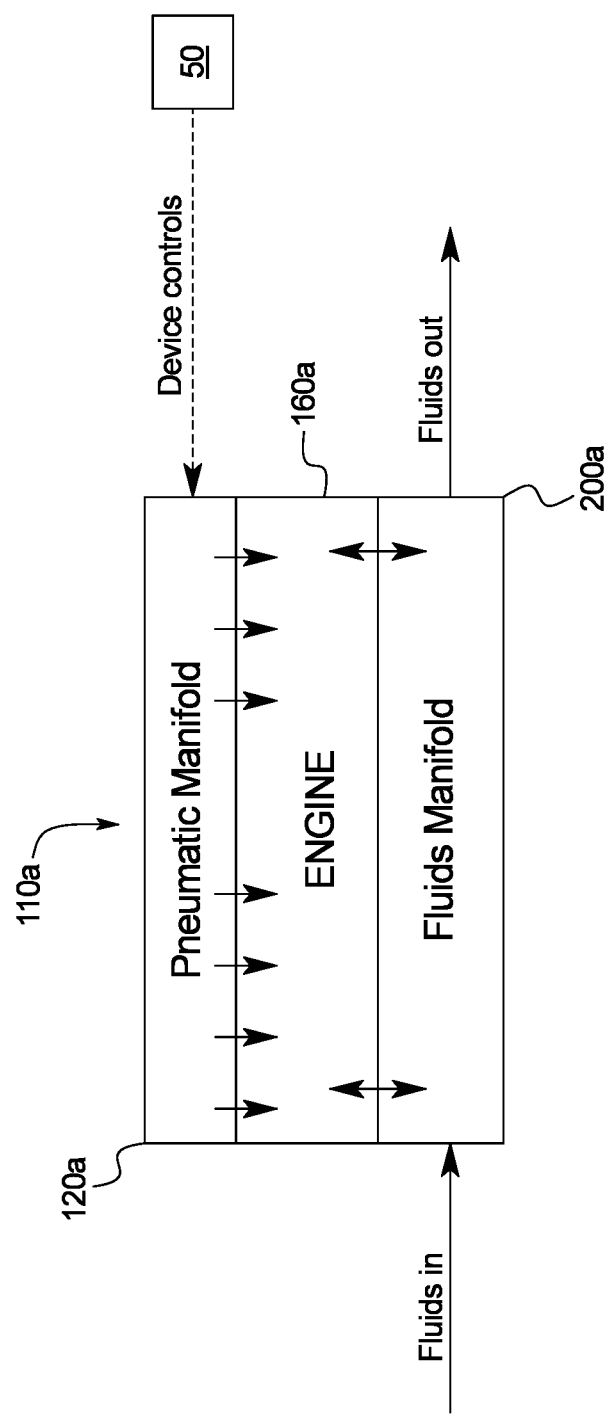
FIG. 13 is a schematic elevation view of the medical fluid management assembly of FIG. 3.

Referring now to FIG. 13, a schematic cross-sectional view of fluid management assembly 110a described above in connection with FIG. 3 is illustrated. Medical fluid management assembly 110a includes pneumatic manifold 120a, pump and valve engine 160a, and fluid manifold 200a as described above including all structure, functionality and alternatives. In various embodiments, pneumatic manifold 120a may be affixed to a chassis of machine 90 (FIG. 1), while pump and valve engine 160a and fluid manifold 200a are removed from pneumatic manifold 120a for periodic replacement. Pump and valve engine 160a and fluid manifold 200a may for example be accessed from the front, back or one of the left or right sides of machine 90.

Figure 14:
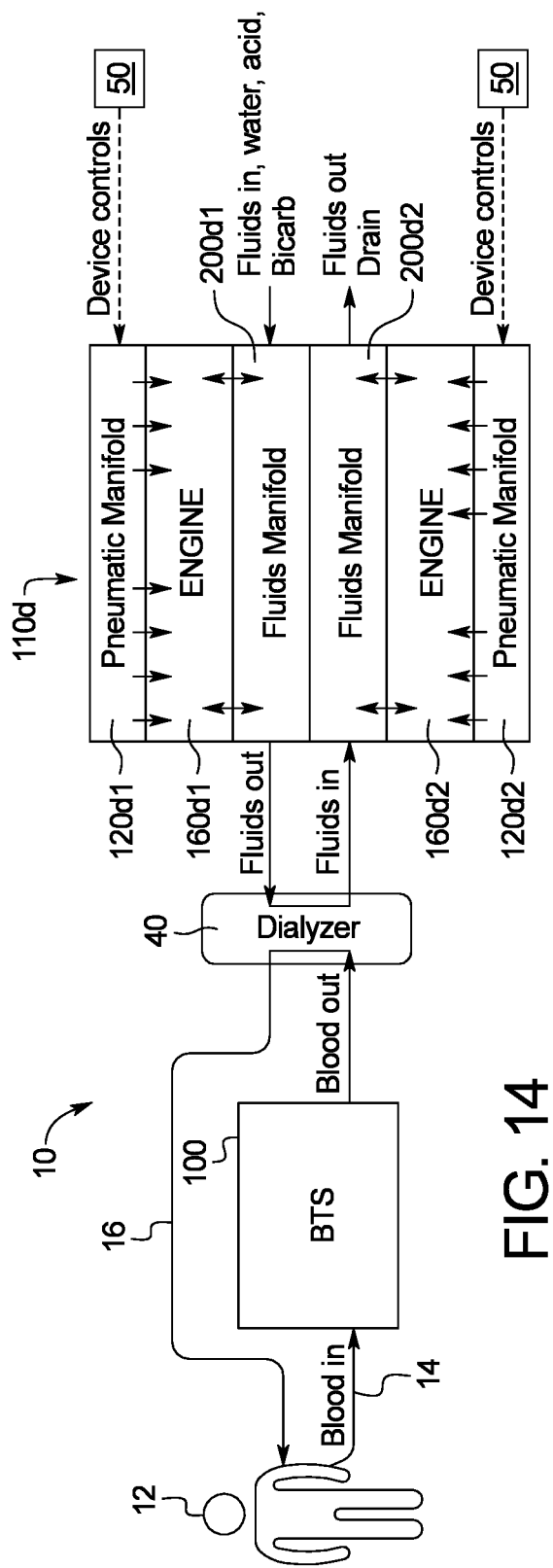
FIG. 14 is a schematic elevation view of another embodiment for a medical fluid management assembly of the present disclosure operating in a renal failure therapy system.

Referring now to FIG. 14, one embodiment of a further alternative fluid management assembly 110d operating in a renal failure therapy system, such as system 10 (FIG. 1) is illustrated schematically. Here, dual fluid manifolds 200d1 and 200d2 are aligned back to back. First fluid manifold 200d1 operates with a first pneumatic manifold 120d1 and a first pump and valve engine 160d1 according to any of the disclosure provided herein, while second fluid manifold 200d2 operates with a second pneumatic manifold 120d2 and a second pump and valve engine 160d2 according to any of the disclosure provided herein. In alternative embodiments, parts or all of one or both of first pump and valve engine 160d1 and second pump and valve engine 160d2 are removed according to FIGS. 4 and 5.

First pneumatic manifold 120d1 and second pneumatic manifold 120d2 may be hingedly connected to the chassis of machine 90, such that they may hinge away from each other, carrying their respective pump and valve engines and fluid manifolds away from each other for replacement. Once replaced, first pneumatic manifold 120d1 and second pneumatic manifold 120d2 are brought together hingedly. First pneumatic manifold 120d1 and second pneumatic manifold 120d2 are operably connected to control unit 50 for valve operation and sensor reading in the illustrated embodiment.

In FIG. 14, first fluid manifold 200d1 takes water, acid and bicarb in and includes all components from the left end to ultrafilter 78 in FIG. 12 to output purified dialysis fluid to dialyzer 40. Second fluid manifold 200d2 takes used dialysis fluid in from dialyzer 40 and includes all components from balance chambers 86a, 86b to UF pump 104 in FIG. 12 to output used dialysis fluid to drain. Blood set 100 (FIG. 2) is provided separately from fluid management assembly 110d and pumps blood under negative pressure from patient 12 along arterial line 14, through dialyzer 40 (counterflow to dialysis fluid in one embodiment), and returns blood to patient 12 under positive pressure via venous line 16.

Figure 15:
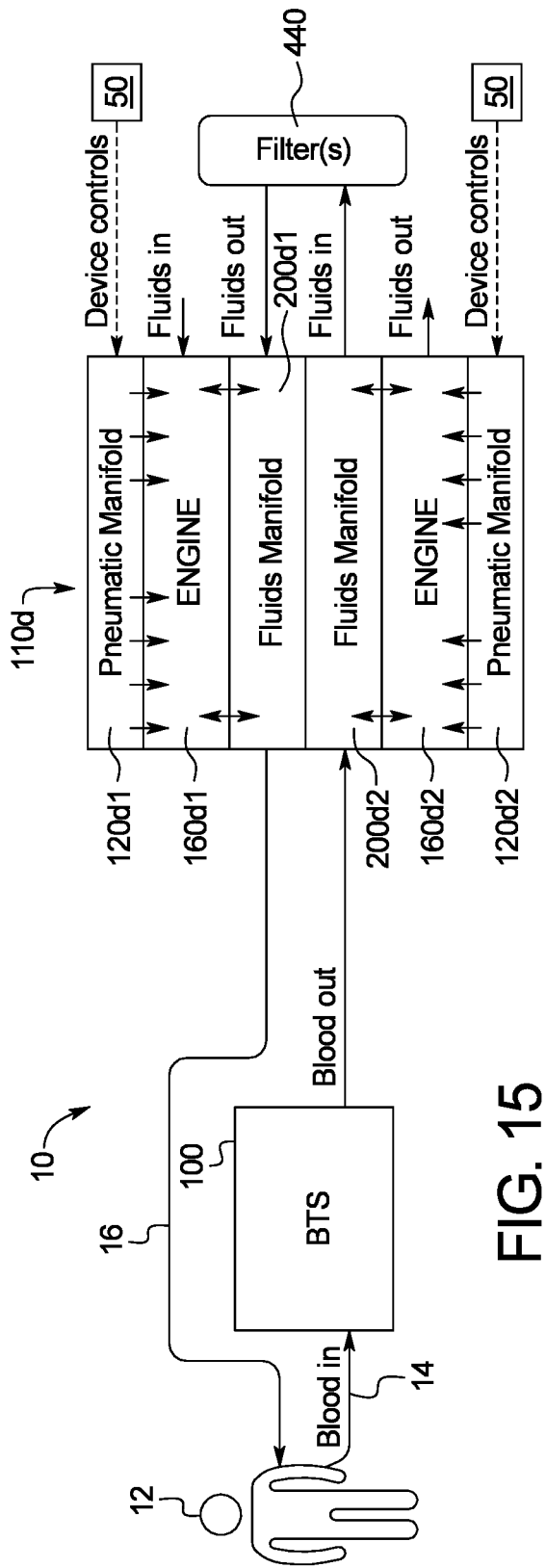
FIG. 15 is a schematic elevation view of the medical fluid management assembly of FIG. 14 performing an alternative direct blood or medical fluid treatment.

Referring now to FIG. 15, the same fluid management assembly 110d (including all structure, functionality and alternatives described or incorporated by reference above in FIG. 14) may be used for a different blood treatment, e.g., providing hemofiltration for sepsis. Blood set 100 (FIG. 2) is again provided separately from fluid management assembly 110d and pumps blood under negative pressure from patient 12 along arterial line 14, and into second fluid manifold 200d2, which pumps the blood through a sepsis filter 440 and into first fluid manifold 200d1, which returns blood to patient 12 under positive pressure via venous line 16.

Figure 16:
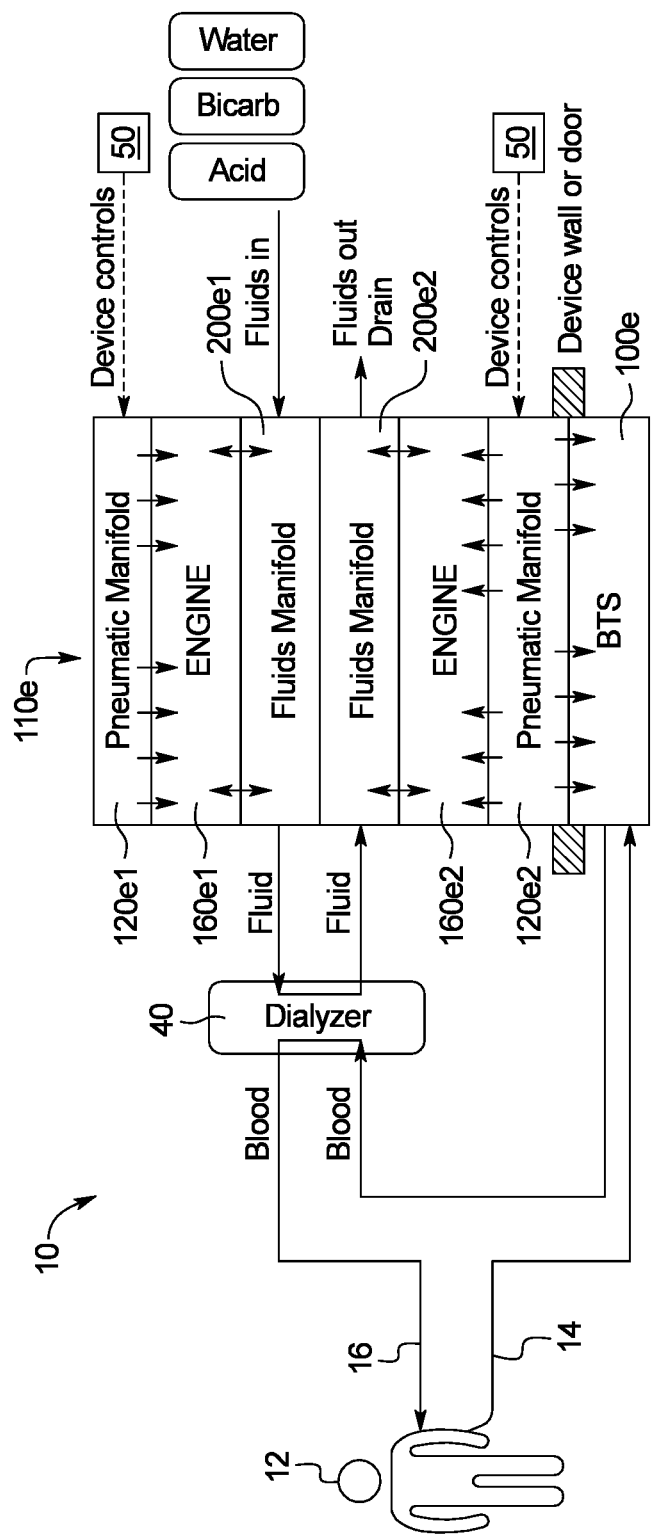
FIG. 16 is a schematic elevation view of a further embodiment for a medical fluid management assembly of the present disclosure operating in a renal failure therapy system.

Referring now to FIG. 16, an embodiment of still a further alternative fluid management assembly 110e operating in a renal failure therapy system, such as system 10 (FIG. 1) is illustrated schematically. Here again, dual fluid manifolds 200e1 and 200e2 are aligned back to back. First fluid manifold 200e1 operates with a first pneumatic manifold 120e1 and a first pump and valve engine 160e1 according to any of the disclosure provided herein, while second fluid manifold 200e2 operates with a second pneumatic manifold 120e2 and a second pump and valve engine 160e2 according to any of the disclosure provided herein. In alternative embodiments, parts or all of one or both of first pump and valve engine 160e1 and second pump and valve engine 160e2 are removed according to FIGS. 4 and 5.

First pneumatic manifold 120e1 and second pneumatic manifold 120e2 may again be hingedly connected to the chassis of machine 90 for component replacement. First and second pneumatic manifolds 120e1 and 120e2 are operably connected to control unit 50 for valve operation and sensor reading in the illustrated embodiment. In FIG. 16, first fluid manifold 200e1 receives water, acid and bicarb in and includes all components from the left end to ultrafilter 78 in FIG. 12 to output purified dialysis fluid to dialyzer 40. Second fluid manifold 200e2 receives used dialysis fluid in from dialyzer 40 and includes all components from balance chambers 86a, 8cb to the right end of FIG. 12, including blood pump 30 and heparin pump 24. Blood set 100 (FIG. 2) is here incorporated into fluid management assembly 110e. The incorporated blood pump 30 pumps blood under negative pressure from patient 12 along arterial line 14, through dialyzer 40 (counterflow to dialysis fluid in one embodiment), and returns the blood to patient 12 under positive pressure via venous line 16.

In an embodiment, first pneumatic manifold 120e1 and second pneumatic manifold 120e1 are mounted to the chassis of machine 90 (FIG. 1) such that they may slide away from each other. First pneumatic manifold 120e1 carries first pump and valve engine 160e1 and first fluid manifold 200e1, while second pneumatic manifold 120e2 carries second pump and valve engine 160e2, second fluid manifold 200e2 and blood set components 30 and 24, such that once apart the (i) first pump and valve engine 160e1 and first fluid manifold 200e1 may be replaced as needed and (ii) second pump and valve engine 160e2, second fluid manifold 200e2 and blood set components 30 and 24 may be replaced as needed. Once replacement is completed, first pneumatic manifold 120e1 and second pneumatic manifold 120e1 are slid back together along the chassis.

FIG. 16 also illustrates blood set 100e (including all structure, functionality and alternatives discussed above in connection with blood set 100 shown of FIG. 2. Blood set 100e is illustrated on the outside of fluid management assembly 110e, mated to pneumatic manifold 120e2. Such arrangement simplifies architecture, reduces number of parts, etc. Blood set 100e may be replaced frequently and may therefore be placed on the outside of chassis of machine 90, e.g., on its wall or door, where it is visible and accessible (e.g., snapped into and out of place). Pump and valve engines 160e1 and 160e2 and pneumatic manifolds 120e1 and 120e2 of fluid management assembly 110e may be permanent or replaced infrequently, e.g., once every six months or longer, and are located accordingly within the chassis of machine 90.

Referring now to FIG. 17, one embodiment of a yet another alternative fluid management assembly 110f is illustrated schematically. Here again, dual fluid manifolds 200f1 and 200f2 are aligned back to back. First fluid manifold 200f1 operates with a first pneumatic manifold 120f1 and multiple pump and valve engines 160f2, 160f3 and 160f4 according to any of the disclosure provided herein, while second fluid manifold 200f2 operates with a second pneumatic manifold 120f2 and a first pump and valve engine 160f1 according to any of the disclosure provided herein. In alternative embodiments, parts or all of one or more or all of first to fourth pump and valve engines 160f1 to 160f4 are removed according to FIGS. 4 and 5.

First pneumatic manifold 120d1 and second pneumatic manifold 120d2 may be hingedly connected to the chassis of machine 90 for component removal as discussed above. First pneumatic manifold 120d1 and second pneumatic manifold 120d2 are operably connected to control unit 50 for valve operation and sensor reading in the illustrated embodiment. Control unit 50 may control the electrical and signal functionality for all of machine 90 and system 10.

FIG. 17 is a cross-sectional view illustrating that there does not have to be a one-to-one relationship between pneumatic manifolds, pump and valve engines and fluid manifolds. For a single pneumatic manifold there may be: (i) a single fluid manifold, (ii) a single fluid manifold and a single pump and valve engine, (iii) a single fluid manifold and a multiple pump and valve engines, (iv) multiple fluid manifolds and a single pump and valve engine, and (v) multiple fluid manifolds and multiple pump and valve engines. For a single pump and valve engine there may be: (i) a single pneumatic manifold and multiple fluid manifolds, (ii) multiple pneumatic manifolds and a single fluid manifold, and (iii) multiple pneumatic manifolds and multiple fluid manifolds. For a single fluid manifold there may be: (i) a single pneumatic manifold and multiple pump and valve engines, (ii) multiple pneumatic manifolds and a single pump and valve engine, and (iii) multiple pneumatic manifolds and multiple pump and valve engines.

FIG. 17 illustrates the modularity of fluid management assembly 110f. As illustrated, different pump and valve engines may be attached to the same fluid manifolds to achieve different functionality.

Referring now to FIGS. 18A to 18C, the modularity of the fluid management assemblies of the present disclosure are illustrated schematically by fluid management assemblies 110g1 to 110g3. Each of fluid management assemblies 110g1 to 110g3 includes a different fluid manifold 200g1, 200g2 and 200g3, respectively. Each of fluid management assemblies 110g1 to 110g3 includes a same first pump and valve engine 160g1. Fluid management assembly 110g1 additionally includes second and third pump and valve engines 160g2 and 160g3. Fluid management assembly 110g2 additionally includes second and fourth pump and valve engines 160g2 and 160g4. Fluid management assembly 110g3 additionally includes second, third and fourth pump and valve engines 160g2, 160g3 and 160g4. It should therefore be appreciated that different ones of the same pneumatic manifolds, the same pump and valve engines, and the same fluid manifolds may be mixed and matched in a modular manner to produce different overall fluid management assemblies, each having a desired functionality.

Figure 19A:
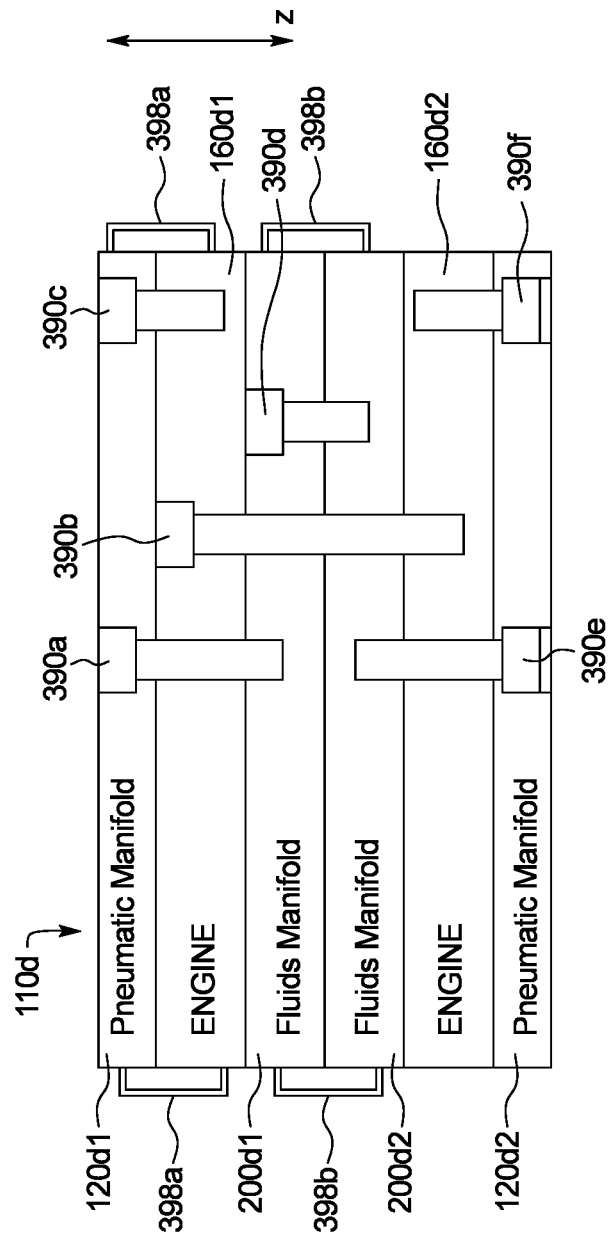
FIGS. 19A and 19B are schematic elevation and top/bottom views, respectively, illustrating alternative fastening structure used with the example medical fluid management assembly of FIGS. 14 and 15.
Figure 19B:
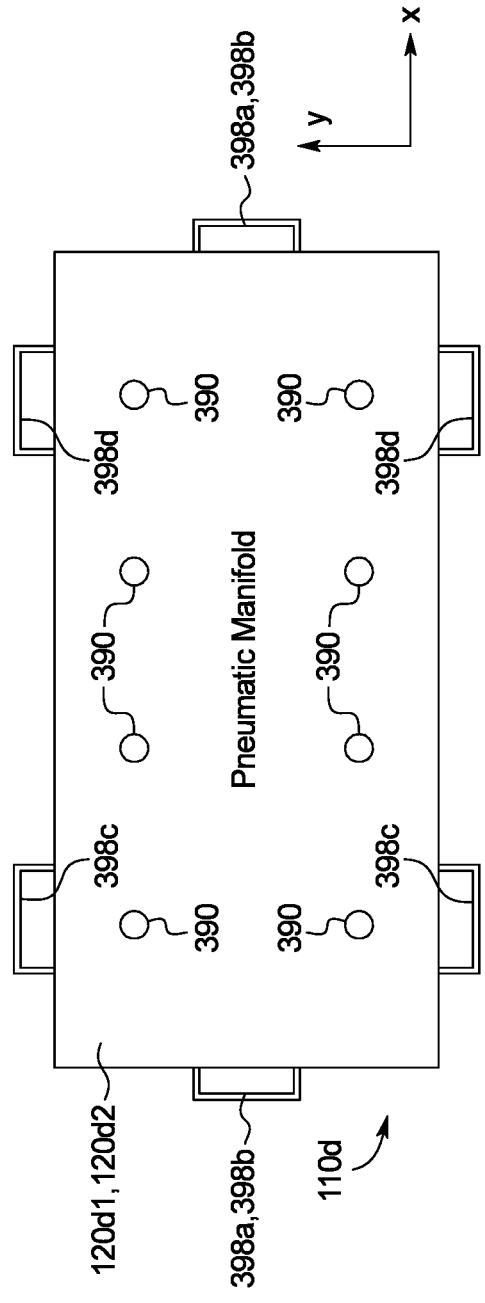

Referring now to FIGS. 19A and 19B, fluid management assembly 110d discussed above is shown with additional attachment detail, which is applicable to any of the medical fluid management assemblies of the present disclosure. FIG. 10 and associated text describe bolts or fasteners 390 and 394 used to hold the fluid management assemblies of the present disclosure releaseably together. FIG. 19A further describes that multiple bolts or fasteners 390a to 390f may be used to hold two or more of any of a pneumatic manifold, a pump and valve engine, and a fluid manifold together. Where bolts or fasteners 390a to 390f thread into a plastic component, a threaded metal insert may be formed into or adhered to the plastic component, so that a desired amount of tightness may be achieved without cracking the plastic component.

In the illustrated embodiment, bolt or fastener 390a holds pneumatic manifold 120d1, pump and valve engine 160d1 and fluid manifold 200d1 releaseably together. Bolt or fastener 390b holds pump and valve engine 160d1, fluid manifold 200d1, fluid manifold 200d2 and pump and valve engine 160d2 releaseably together. Bolt or fastener 390c holds pneumatic manifold 120d1 and pump and valve engine 160d1 releaseably together. Bolt or fastener 390d holds fluid manifold 200d1 and fluid manifold 200d2 releaseably together. Bolt or fastener 390e holds pneumatic manifold 120d2, pump and valve engine 160d2 and fluid manifold 200d2 releaseably together. Bolt or fastener 390f holds pneumatic manifold 120d2 and pump and valve engine 160d2 releaseably together.

Removing outer bolts or fasteners 390a, 390c, 390e and 390f allows access to inner bolts or fasteners 390b and 390d. In this order, fluid management assembly 110d may be deconstructed easily to replace any necessary components. Reversing that order enables fluid management assembly 110d with replaced components to be easily reconstructed. FIG. 19B illustrates a top or bottom view of fluid management assembly 110d showing that an array of bolts or fasteners may be inserted from outside of pneumatic manifold 120d1 or 120d2, e.g., in an ordered pattern, to ensure that sufficient pneumatic pressure is distributed evenly along the entire fluid management assembly to ensure that all gastketing and o-ring seals are adequately compressed for proper sealing.

FIGS. 19A and 19B further illustrate that mechanical fast release clamps 398a, 398b, 398c and 398d may be used to hold pneumatic manifolds 120d1, 120d2, pump and valve engines 160d1, 160d2 and fluid manifolds 200d1, 200d2 releaseably together in x-y directions (where bolts or fasteners 390a to 390f clamp in a z-direction), which properly aligns the various chambers, flexible membranes 190, 192, o-rings 144, and sheet gasketing releaseably in place prior to z-direction clamping via fasteners 390a to 390f and/or the structure and methodology discussed in connection with FIG. 10. Fast release clamps 398a, 398b, 398c and 398d may be used exclusively or together with bolts and/or other fasteners.

It should be understood that various changes and modifications to the presently preferred embodiments described herein will be apparent to those skilled in the art. Such changes and modifications can be made without departing from the spirit and scope of the present subject matter and The invention is claimed as follows:

1. A medical fluid management assembly comprising:
   a pneumatic manifold in pneumatic communication with a source of pneumatic pressure, the pneumatic manifold including a plurality of pneumatic passageways and a plurality of pneumatic connectors;
   a valve engine including a valve chamber, the valve engine including a first pneumatic connector mated sealingly and releaseably with one of the pneumatic connectors of the pneumatic manifold, the valve engine further including a valve fluid connector;
   a pump engine including a pump chamber, the pump engine including a second pneumatic connector mated sealingly and releaseably with another one of the pneumatic connectors of the pneumatic manifold, the pump engine further including a pump fluid connector; and
   a fluid manifold including a plurality of fluid pathways and a plurality of fluid connectors mated sealingly and releaseably with the respective fluid connectors of the valve engine and the pump engine, the fluid manifold being fluidly coupled to at least one of a purified water line, a liquid concentrate line, a to—extracorporeal circuit fresh dialysis fluid line, a drain line, or a from—extracorporeal circuit used dialysis fluid line.

2. The medical fluid management assembly of claim 1, further comprising a second valve engine including a second valve chamber, the second valve engine including a third pneumatic connector mated sealingly and releaseably with another one of the pneumatic connectors of the pneumatic manifold, the second valve engine further including a second valve fluid connector that is mated sealingly and releaseably with one of the plurality of fluid connectors of the fluid manifold.

3. The medical fluid management assembly of claim 1, wherein at least one of the valve engine or the pump engine is included within a fluid pumping cassette that is removeably attached to the pneumatic manifold.

4. The medical fluid management assembly of claim 1, wherein the pneumatic manifold includes a plurality of plates mated together, at least one of the plates defining grooves forming the plurality of pneumatic passageways.

5. The medical fluid management assembly of claim 1, wherein each of the valve engine and the pump engine includes first and second rigid plates at least partially separated by at least one flexible membrane.

6. The medical fluid management assembly of claim 5, wherein the first and second rigid plates are separated at areas defining the pump chamber and the valve chamber by the at least one flexible membrane.

7. The medical fluid management assembly of claim 6, wherein the first and second rigid plates further define at least one of a balance chamber, a water accumulation chamber, a mixing chamber, a water deaeration chamber or a dialysis fluid deaeration chamber.

8. The medical fluid management assembly of claim 1, wherein the valve engine and the pump engine are collectively configured to mix purified water received from a purified water line and concentrate received from a liquid concentrate line in the pump chamber.

9. The medical fluid management assembly of claim 1, wherein the valve engine is integrally formed with the pump engine.

10. The medical fluid management assembly of claim 1, wherein the pneumatic manifold further includes at least one pneumatic source connector for connecting with the source of pneumatic pressure.

11. The medical fluid management assembly of claim 1, wherein the first pneumatic connector of the valve engine and the second pneumatic connector of the pump engine are ports that mate with the plurality of pneumatic connectors of the pneumatic manifold, which include recesses.

12. The medical fluid management assembly of claim 11, wherein the pneumatic manifold provides o-ring seals that extend around or within the recesses to seal against the respective ports of the pump engine and the valve engine.

13. The medical fluid management assembly of claim 1, wherein the pump fluid connector of the pump engine and the valve fluid connector of the valve engine are ports that mate with the plurality of fluid connectors of the fluid manifold, which include recesses.

14. The medical fluid management assembly of claim 13, wherein the fluid manifold provides o-ring seals that extend around or within the recesses to seal against the respective ports of the pump engine and the valve engine.

15. The medical fluid management assembly of claim 1, further comprising a plurality of pressure valves, each pressure valve provided along or fluidly coupled to one of the plurality of pneumatic passageways; and
   a control unit electrically coupled to the plurality of pressure valves, the control unit configured to separately control each of the pressure valves to regulate pneumatic pressure provided to the pump chamber and the valve chamber.

16. The medical fluid management assembly of claim 1, further comprising a fluid tube that fluidly connects the valve chamber with the pump chamber.

17. A medical fluid management assembly comprising:
   a pneumatic manifold in pneumatic communication with a source of pneumatic pressure, the pneumatic manifold including a plurality of pneumatic passageways and a plurality of pneumatic connectors;
   a first valve engine including a first valve chamber, the first valve engine including a first pneumatic connector mated sealingly and releaseably with one of the pneumatic connectors of the pneumatic manifold, the first valve engine further including a first valve fluid connector;
   a second valve engine including a second valve chamber, the second valve engine including a second pneumatic connector mated sealingly and releaseably with another one of the pneumatic connectors of the pneumatic manifold, the second valve engine further including a second valve fluid connector;
   a pump engine including a balance chamber, the pump engine including a third pneumatic connector mated sealingly and releaseably with another one of the pneumatic connectors of the pneumatic manifold, the pump engine further including a pump fluid connector; and
   a fluid manifold including a plurality of fluid pathways and a plurality of fluid connectors mated sealingly and releaseably with the respective fluid connectors of the first valve engine, the second valve engine, and the pump engine, the fluid manifold being fluidly coupled to at least one of a purified water line, a liquid concentrate line, a to—extracorporeal circuit fresh dialysis fluid line, a drain line, or a from—extracorporeal circuit used dialysis fluid line.

18. The medical fluid management assembly of claim 17, wherein the first valve engine is located upstream from the pump engine and the second valve engine is located downstream from the pump engine.

19. The medical fluid management assembly of claim 17, further comprising:
   a first fluid tube that fluidly connects the first valve chamber with the balance chamber; and
   a second fluid tube that fluidly connects the second valve chamber with the balance chamber.

20. The medical fluid management assembly of claim 17, wherein at least one of the first valve engine, the second valve engine, or the pump engine is included within a fluid pumping cassette that is removeably attached to the pneumatic manifold.

* * * * *